United States Patent
Sakuta et al.

(10) Patent No.: US 8,592,547 B2
(45) Date of Patent: Nov. 26, 2013

(54) ORGANOPOLYSILOXANE, A METHOD OF PREPARING THE SAME AND A COSMETIC COMPRISING THE SAME

(75) Inventors: Koji Sakuta, Annaka (JP); Kiyomi Tachibana, Tokyo (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 181 days.

(21) Appl. No.: 12/894,974

(22) Filed: Sep. 30, 2010

(65) Prior Publication Data

US 2011/0015337 A1    Jan. 20, 2011

Related U.S. Application Data

(62) Division of application No. 12/081,075, filed on Apr. 10, 2008, now abandoned.

(30) Foreign Application Priority Data

Jun. 18, 2007    (JP) .................................. 2007-160666

(51) Int. Cl.
C08G 77/12    (2006.01)

(52) U.S. Cl.
USPC .................................. 528/31; 528/32; 528/25

(58) Field of Classification Search
USPC .............................................. 528/31, 32, 25
See application file for complete search history.

(56) References Cited

U.S. PATENT DOCUMENTS

| | | | |
|---|---|---|---|
| 4,987,169 A | 1/1991 | Kuwata et al. | |
| 5,236,986 A | 8/1993 | Sakuta et al. | |
| 5,412,004 A | 5/1995 | Tachibana et al. | |
| 6,013,711 A | 1/2000 | Lewis et al. | |
| 6,238,657 B1 | 5/2001 | Lin et al. | |
| 6,476,123 B1 | 11/2002 | Morita et al. | |
| 6,576,623 B1 | 6/2003 | Nakanishi et al. | |
| 2002/0114771 A1 | 8/2002 | Nakanishi | |
| 2003/0064046 A1 | 4/2003 | Omura et al. | |
| 2004/0234477 A1 | 11/2004 | Sakuta | |
| 2006/0034875 A1 | 2/2006 | Nakanishi et al. | |

FOREIGN PATENT DOCUMENTS

| EP | 1 426 027 A1 | 6/2004 |
|---|---|---|
| EP | 1 550 687 A1 | 7/2005 |
| JP | 2-43263 A | 2/1990 |
| JP | 4-268376 A | 9/1992 |
| JP | 4-272932 A | 9/1992 |
| JP | 5-140320 A | 6/1993 |
| JP | 9-136813 A | 6/1997 |
| JP | 10-245313 A | 9/1998 |
| JP | 11-1615 A | 1/1999 |
| JP | 11-71460 A | 3/1999 |
| JP | 2000-26737 A | 1/2000 |
| JP | 2001-2521 A | 1/2001 |
| JP | 2001-39819 A | 2/2001 |
| JP | 2001-40097 A | 2/2001 |
| JP | 2001-48729 A | 2/2001 |
| JP | 2001-64513 A | 3/2001 |
| JP | 2002-29921 A | 1/2002 |
| JP | 2002-179548 A | 6/2002 |
| JP | 2004-300227 A | 10/2004 |
| JP | 2004-307371 A | 11/2004 |
| KR | 2001-0007444 | 1/2001 |
| WO | WO 03/024413 A1 | 3/2003 |
| WO | WO 2004/024798 A1 | 3/2004 |

OTHER PUBLICATIONS

JP 10 245313 Machine translation (1998).*
Office Action dated Aug. 16, 2011 for Japanese Application No. 2009-090561.
Office Action dated Jan. 7, 2011 for Korean Application No. 10-2008-0038111.
The European Search Report for European Patent Appl. No. 08154170.8 dated Jul. 9, 2009.
Koji Sakuta, J. Soc. Cosmet. Chem. Jpn., 27(3), pp. 480-483 (1993).

* cited by examiner

Primary Examiner — Kuo-Liang Peng
(74) Attorney, Agent, or Firm — Birch, Stewart, Kolasch & Birch, LLP

(57) ABSTRACT

An organopolysiloxane having a main chain composed of the following repeating units (I), 2 to 199 side chain units (II) and 1 to 50 crosslinkage units (III) per 100 SiO units in the main chain, provided that the organopolysiloxane has at least 2, on average, crosslinkage units (III):

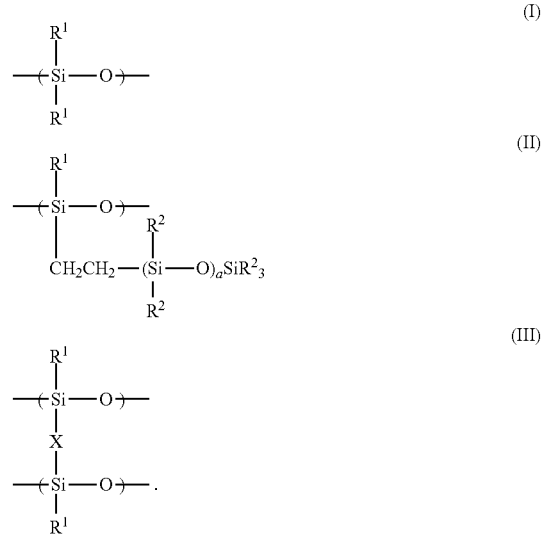

8 Claims, No Drawings

ORGANOPOLYSILOXANE, A METHOD OF PREPARING THE SAME AND A COSMETIC COMPRISING THE SAME

CROSS REFERENCE

The present application is a 37 C.F.R. §1.53(b) divisional of, and claims priority to, U.S. application Ser. No. 12/081,075, filed Apr. 10, 2008 now abandoned. Priority is also claimed to Japanese Patent Application No. 2007-160666 filed on Jun. 18, 2007. The entire contents of each of these applications is hereby incorporated by reference.

FIELD OF THE INVENTION

The present invention relates to an organopolysiloxane, a method of preparing the same and a cosmetic comprising the same. The organopolysiloxane of the present invention has specific amounts of side chains and crosslinkages, and thickens not only silicone oils but also other kinds of oils or unctuous agents to form paste compositions having no greasiness. It can also form an emulsion depending on structures of the side chains and the crosslinkages. The present method of preparing the organopolysiloxane comprises two steps, i.e., the first step to form the side chain and the second step to form the crosslinkage, enables one to prepare the organopolysiloxane having specific amounts of side chains and crosslinkages.

PRIOR ART

Silicone oils are used as base oils in various applications such as cosmetic because they are safe to the human skin. Particularly, for skin care and makeup cosmetics, silicone oils having a low viscosity of 100 mm²/s or lower are widely used for the reasons that they are safe, spread smoothly, and give refreshing feel to the skin. However, due to the low viscosity, relatively large amount of a thickener is required to form a paste composition from the silicone oil. It is sometimes difficult to obtain a paste which is stable and homogeneous with no breed out of the silicone oil.

As a thickener for a low viscosity silicone, the Japanese Patent Application Laid-Open No. H02-43263 discloses a method of preparing a homogeneous paste composition by kneading a specific silicone polymer thickener and a low viscosity silicone under shear. It is known that significantly improved thickening effect can be attained by adding inert silicone oil during a production process of a silicone polymer according to J. Soc. Cosmet. Chem. Jpn., 27(3), 480-483 (1993) regarding a method of preparing a silicone thickener and thickening effect thereof. However, addition of a large amount of the silicone oil causes greasiness of the paste applied to the skin.

Many cosmetics comprise not only oil components but also water. The aforesaid silicone polymer is difficult to disperse in such water-containing cosmetics.

To improve dispersion of silicone oils in water, the Japanese Patent Application Laid-Open No. H04-272932 and H05-140320 describe introducing a polyoxyalkylene group in silicone thickeners, and International Patent Publication WO/04-024798 describes introducing a polyglycerin moiety in a silicone thickener. However, these thickeners do not have good compatibility with unctuous agents other than silicone oil, for example, hydrocarbon oils and ester oils.

The Japanese Patent Application Laid-Open No. H09-136813 and International Patent Publication WO/04-24413 describe silicone thickeners which have long-chain alkyl groups to have good compatibility with hydrocarbon oils and ester oils. However, they do not thicken silicone oils satisfactorily.

SUMMARY OF THE INVENTION

An object of the present invention is to provide an organopolysiloxane polymer and a method of preparing the polymer which polymer has good compatibility not only with silicone oils but also other kinds of organic oils to form paste compositions having no greasiness.

The present invention is an organopolysiloxane having a main chain composed of the following repeating units (I), 2 to 199 side chain units (II) and 1 to 50 crosslinkage units (III) per 100 SiO units in the main chain, provided that the organopolysiloxane has at least 2, on average, crosslinkage units (III),

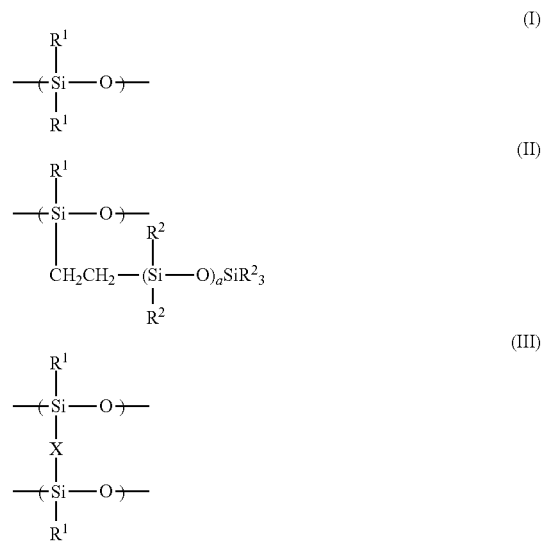

wherein $R^1$ may be the same with or different from each other and is an organic group selected from the group consisting of substituted or unsubstituted $C_{1-30}$ hydrocarbon groups having no aliphatic unsaturated bond, a group represented by the formula, $-C_jH_{2j}O(C_kH_{2k}O)_bR^4$, wherein j is an integer of from 2 to 20, k is an integer of from 2 to 4, b is an integer of from 2 to 100, $R^4$ is a hydrogen atom, a substituted or unsubstituted $C_{1-30}$ hydrocarbon group or an acetyl group, and a group represented by the formula, $-C_gH_{2g}$ $OCH_2CH(OH)CH_2O(CH_2CH(OH)CH_2O)_cR^4$, wherein g is an integer of from 2 to 20 and c is an integer of from 0 to 10, $R^2$ may be the same with or different from each other and is a substituted or unsubstituted $C_{1-30}$ hydrocarbon group having no aliphatic unsaturated bond, a is an integer of from 1 to 300, X is selected from the group consisting of an ethylene group and groups represented by the following formula (IV), (V), (VI), or (VII)

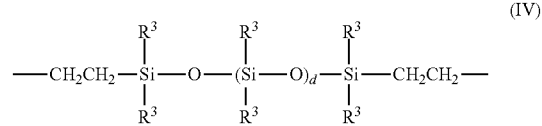

-continued

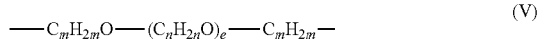  (V)

  (VI)

  (VII)

wherein $R^3$ may be the same with or different from each other and is a substituted or unsubstituted $C_{1-30}$ hydrocarbon group having no aliphatic unsaturated bond, d is an integer of from 0 to 500, e is an integer of from 2 to 100, f is an integer of from 0 to 10, m is an integer of from 2 to 20, n is an integer of from 2 to 4, and p is an integer of from 4 to 20.

The present invention also provides a paste composition and a cosmetic comprising the aforesaid organopolysiloxane.

In addition, the present invention provides a method suitable for preparing the organopolysiloxane.

The organopolysiloxane of the present invention has specific amounts of side chains and crosslinkages to be able to thicken not only silicone oils but also other kinds of oils. It can also form a stable emulsion. The organopolysiloxane of the present invention is very useful for cosmetics comprising a mixture of different types of unctuous agents and water.

PREFERRED EMBODIMENTS OF THE INVENTION

The aforesaid repeating unit (I) constitutes a main chain of the organopolysiloxane of the present invention. In the repeating unit (I), $R^1$ is an organic group selected from substituted or unsubstituted $C_{1-30}$ hydrocarbon groups having no aliphatic unsaturated bond, a group represented by the formula, $-C_jH_{2j}O(C_kH_{2k}O)_bR^4$, and a group represented by the formula, $-C_gH_{2g}OCH_2CH(OH)CH_2O(CH_2CH(OH)CH_2O)_cR^4$. A plurality of $R^{1'}$ may be different from each other.

Examples of the hydrocarbon group as $R^1$ include alkyl groups such as methyl, ethyl, propyl, butyl, pentyl, hexyl, heptyl, octyl, nonyl, decyl, stearyl, and behenyl groups; alicyclic groups such cyclopentyl and cyclohexyl group; aryl groups such as phenyl and tolyl groups; aralkyl groups such as phenetyl group; and fluorinated alkyl groups such as trifluoropropyl, nonafluorohexyl, and heptyldecylfluorodecyl groups. Preferably, 50 to 95 mole % of $R^1$ is a methyl group and 50 to 5 mole % of $R^1$ is a hydrocarbon group, particularly an alkyl or aryl group, having 6 to 30, preferably 6 to 22, and more preferably 8 to 18 carbon atoms.

In the formula, $-C_jH_{2j}O(C_kH_{2k}O)_bR^4$, j is an integer of from 2 to 20, preferably from 3 to 12, k is an integer of from 2 to 4, and b is an integer of from 2 to 100, preferably from 5 to 50. $R^4$ is a hydrogen atom, $C_{1-30}$ hydrocarbon group, which may be substituted, or an acetyl group. In the formula, $-C_gH_{2g}OCH_2CH(OH)CH_2O(CH_2CH(OH)CH_2O)_cR^4$, g is an integer of from 2 to 20, preferably from 3 to 12, and c is an integer of from 0 to 10, preferably from 1 to 4. Example of $R^4$ include alkyl groups such as methyl, ethyl, propyl, butyl, pentyl, hexyl, heptyl, octyl, nonyl, decyl, stearyl, and behenyl groups and acetyl group, among which a hydrogen atom, methyl, butyl and acetyl groups are preferred.

The side chain (II) comprises an organopolysiloxane moiety grafted to the aforesaid main chain, $R^1SiO$, via a silethylene group. The side chain (II) can be formed by subjecting an organopolysiloxane to constitute the main chain and an organovinylpolysiloxane represented by the formula (XII) to an addition reaction before forming the after-mentioned crosslinkage (III), wherein the alkylhydrogensiloxane comprises at least three, per molecule, alkylhydrogensiloxane unit of the formula, $-(Si(R^1)(H)O)-$.

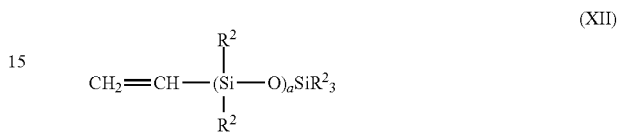  (XII)

Alternatively, the side chain (II) can be formed by subjecting an organopolysiloxane to constitute the main chain and an organohydrogenpolysiloxane represented by the formula (XIII) to an addition reaction, wherein the organopolysiloxane has alkylvinylsiloxane units of the formula, $-(Si(R^1)(CH=CH_2)O)-$.

  (XIII)

It is difficult to form a desired number of the side chains (II) and the crosslinkage (III) simultaneously, which will be discussed later.

$R^2$ is a $C_{1-30}$ hydrocarbon group having no aliphatic unsaturated bonds. $R^2$ may be different from each other and its hydrogen atom may be substituted. Examples of $R^2$ include alkyl groups such as methyl, ethyl, propyl, butyl, pentyl, hexyl, heptyl, octyl, nonyl, decyl, stearyl and behenyl group, among which methyl and butyl groups are preferred. In the formula (II), a is an integer of from 1 to 300, preferably from 5 to 100.

The present organopolysiloxane should have an average of at least 2, per molecule, crosslinkage $-X-$ between $R^1SiO$ and $R^1SiO$, represented by the formula (III). The crosslinkage can be formed by reacting the aforesaid an organopolysiloxane to constitute the main chain with at least one selected from the group consisting of the organopolysiloxane of the following formula (VIII) having vinyl groups, the polyoxyalkylene compound of the following formula (IX), the α, ω-diene compound of the following formula (X), and the (poly)glycerin compound of the following formula (XI), wherein the aforesaid alkylhydrogensiloxane has at least one aforesaid side chain (II) and at least two alkylhydrogensiloxane unit of the formula, $-(Si(R^1)(H)O)-$, per molecule. By the reaction, the aforesaid structures of the formula (IV), (V), (VI), and (VII) are obtained, respectively.

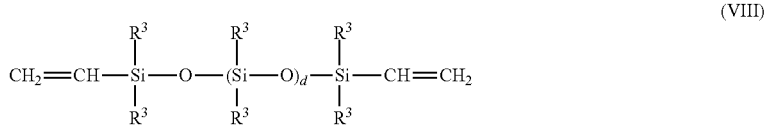  (VIII)

(IX)

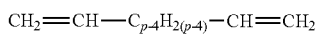

(X)

(XI)

In the above formulas, $R^3$ may be different from each other and is a substituted or unsubstituted $C_{1-30}$ hydrocarbon group having no aliphatic unsaturated bond. $R^8$ and $R^9$ may be different from each other and are hydrogen atoms or methyl groups, d is an integer of from 0 to 500, preferably from 5 to 300, e is an integer of from 2 to 100, preferably from 5 to 70, f is an integer of from 0 to 10, preferably from 1 to 5, m is an integer of from 2 to 20, preferably from 3 to 12, n is an integer of from 2 to 4, and p is an integer of from 4 to 20, preferably from 6 to 16.

An organopolysiloxane having the alkylhydrogensiloxane unit of the formula, $-(Si(R^1)(H)O)-$, is represented by the compositional formula, $R^1{}_qH_rSiO_{(4-q-r)/2}$, wherein q is a number of from 1.2 to 2.5, and r is a number of from 0.001 to 1.0. The organopolysiloxane is preferably linear, but it may have a branch. The hydrogen atoms bonded to silicon atoms may be located at the ends of the organopolysiloxane molecule or the branch.

The organopolysiloxane having a vinyl group is represented by the general formula, $R^3{}_s(CH_2=CH)_tSiO_{(4-s-t)/2}$, wherein $R^3$ may be different from each other and is a substituted or unsubstituted $C_{1-30}$ hydrocarbon group having no aliphatic unsaturated bond, s is a number of from 1.2 to 2.5 and t is a number of from 0.001 to 1.0. Examples of the hydrocarbon group include those listed for $R^2$, and methyl and phenyl groups are preferred. The organopolysiloxane is may be branched, but preferably linear. The vinyl group may be located at the ends of the organopolysiloxane molecule or a branch. The formula (VIII) represents an organopolysiloxane which has vinyl groups only at the ends and does not have any trifunctional siloxanes, i.e., T-units, or tetrafunctional siloxanes, i.e., Q-units.

Besides the aforesaid method, the organopolysiloxane with X represented by the aforesaid formula (IV) can be prepared by use of an organopolysiloxane having an alkylvinylsiloxane unit represented by the formula, $-(Si(R^1)(CH=CH_2)O)-$, to form a main chain and the organohydrogenpolysiloxane represented by the following formula (XIV)

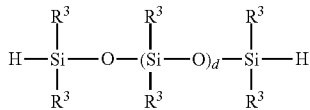

(XIV)

wherein $R^3$ and d are as defined above.

In the present organopolysiloxane, the side chain (II) is contained in an amount of from 2 to 199 units, preferably from 5 to 100 units, per 100 SiO units in the main chain. The crosslinkage (III) is contained in an amount of from 1 to 50 units, preferably from 2 to 30 units, per 100 SiO units in the main chain.

In 100 SiO units in the main chain, $R^1SiO$ unit in the formula (II) and two $R^1SiO$ units in the formula (III) are included, but the one having the substituent $R^2$ and the one having the substituent $R^3$ are not included. An average of at least two crosslinkages (III) should be present per molecule. An organopolysiloxane having less than two crosslinkages (III) may not retain oils satisfactorily. On the other hand, an organopolysiloxane having more than 50 crosslinkages may not be sufficiently swollen with oils. With an organopolysiloxane having less than two side chains (II) per total 100 SiO units in the main chain, high thickening effect and good usability may not be attained at the same time. Moreover, such an organopolysiloxane may not thicken both silicone oils and other kinds of organic oils. The side chains (II) in an amount more than aforesaid upper limit may hinder the formation of the crosslinkage (III). Besides the repeating unit (I), the main chain of the present organopolysiloxane may comprise trifunctional siloxane unit, $R^1SiO_{1.5}$, or tetrafunctional siloxane unit, $SiO_2$, in amounts not to adversely affect the organopolysiloxane.

The present organopolysiloxane can be prepared by subjecting an organopolysiloxane used to form the side chain (II) and an organopolysiloxane used to form a main chain composed of the repeating units (I) to an addition reaction followed by forming the crosslinkage (III). In the process of forming the crosslinkage (III), an unctuous agent or oil may be present to swell the crosslinked product polymer. When an organopolysiloxane having a poly(oxyalkylene) group or (poly) glycerin moiety is prepared, the organopolysiloxane is preferably purified according to a known method, particularly the one described in the International Patent Publication WO/03-20828, after the preparation or formation of a paste composition of the organopolysiloxane.

As described above, the present method comprises the two-steps: addition of the side chain to the main chain organopolysiloxane and then crosslinking. For example, an organohydrogenpolysiloxane having at least three SiH bonds is subjected to an addition reaction with the organopolysiloxane of the aforesaid formula (XII) having a terminal vinyl group and then with a compound having unsaturated bonds at both ends represented by the aforesaid formula (VIII), (IX), (X), or (XI), to form crosslinkage. An organopolysiloxane with side chains and crosslinkages both comprising siloxane moieties can be prepared by addition-reacting an organopolysiloxane having at least three $-Si-CH=CH_2$ groups with the organohydrogenpolysiloxane of the formula (XIII) having a terminal hydrogen atom and then with the organohydrogenpolysiloxane of the formula (XIV) to form crosslinkages.

When the crosslinkage is formed before forming the side chain, efficiency of the addition reaction to form the side chain is significantly low. When the side chain and the crosslinkage are to be formed in a batch reaction, crosslinkages are formed before an intended number of side chains are formed to prevent formation of desired number of side chains, so that properties attained by the side chains may not be obtained.

Comparing reactivity with an organohydrogenpolysiloxane to form the main chain of the organopolysiloxane of the aforesaid formula (XII) and that of the compound of the formula (IX) or (XI) having unsaturated bonds, the former is higher than the latter. Consequently, when the crosslinkages are formed from the compound of the formula (IX) or (XI), an intended organopolysiloxane may be obtained even in a batch process. However, the two-step process is preferred to produce organopolysiloxane having stable quality.

As an organopolysiloxane to form the side chain, an organopolysiloxane having one vinyl group bonded to a non-terminal silicon atom such as 1,1,1,3,5,5,5-heptamethyl-3-vinyltrisiloxane in place of the organopolysiloxane of the aforesaid formula (XII), or an organopolysiloxane having one hydrogen atom bonded to a non-terminal silicon atom such as 1,1,1,3,5,5,5-heptamethyltrisiloxane in place of the organopolysiloxane of the aforesaid formula (XIII) can be used. However, an organopolysiloxane having a terminal vinyl or hydrogen atom is preferred for the reasons that reactivity at the terminal site is higher and a longer side chain is formed.

In the process of producing the polymer of the present invention, an inert silicone oil or organic oil may be present as described in the aforementioned J. Soc. Cosmet. Chem. Jpn., 27(3), 480-483 (1993). The oil can be present either in the process of producing the siloxane side chain or in the process of producing the crosslinkage.

The addition reaction is performed in the presence of a platinum compound such as chloroplatinic acid, chloroplatinic acid modified with an alcohol, or chloroplatinic acid-vinylsiloxane complex, or a rhodium compound at room temperature or an elevated temperature of about 50° C. to 120° C. The reaction may be solventless or performed in the presence of an organic solvent as necessary. Examples of the organic solvent include aliphatic alcohols such as methanol, ethanol, 2-propanol, and butanol; aromatic hydrocarbons such as benzene, toluene, and xylene; aliphatic or alicyclic hydrocarbons such as n-pentane, n-hexane, and cyclohexane; halogenated hydrocarbons such as dichloromethane, chloroform, and carbon tetrachloride; and ketones such as acetone and methyl ethyl ketone. For cosmetic application, solventless reaction or reaction in the presence of ethanol or 2-propanol is preferred.

The organopolysiloxane obtained may be processed to a paste composition by kneading with an unctuous agent which is liquid at room temperature. When the organopolysiloxane is prepared under the presence of a liquid unctuous agent, an additional amount of the liquid unctuous agent can be used to make a paste. Alternatively, the organopolysiloxane may be processed to powder by removing volatile substances and then pulverizing the dried organopolysiloxane. Preferably, the organopolysiloxane is processed to a paste composition which is then incorporated in cosmetics.

To make a paste composition from the organopolysiloxane of the present invention, it is preferred to mix the organopolysiloxane with an unctuous agent which is liquid at room temperature followed by kneading the mixture under shear stress, whereby a paste having a smooth appearance is obtained. Kneading may be performed by a three-roller mill, two-roller mill, side grinder, colloidal mill, Gaulin homogenizer, and DISPER, among which three-roller mill and the DISPER are preferred.

The organopolysiloxane of the present invention can be swollen with a larger weight of oil than that of the organopolysiloxane itself. This can be confirmed by the following method: Kneading, with a three-roller mill, an appropriate weight of the organopolysiloxane and the same weight of a liquid unctuous agent as the organopolysiloxane, then, placing the mixture thus obtained on a 100-mesh net and, after keeping the mixture on the net for 1 hour, confirming that there is no liquid unctuous agent exuded from the mixture.

A liquid oil or unctuous agent having a viscosity of from 0.65 to 10000 mm$^2$/sec at 25° C. is preferred because of their good handling property. Examples of such unctuous agent include silicone oils, hydrocarbon oils, ester oils, animal or plant oils and semi-synthetic oils. When a mixing apparatus capable of uniformly heating contents of the mixer, for example, DISPER mixer, is used, an unctuous agent which is solid at room temperature can be used.

Examples of the silicone oil are as shown below:

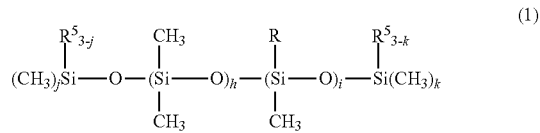

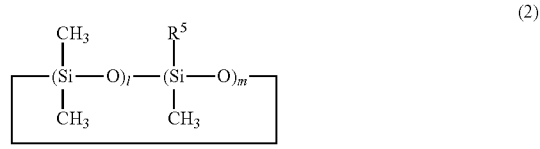

In the formulas (1) and (2), $R^5$ may be the same with or different from each other and is selected from the group consisting of a hydrogen atom, a hydroxyl group, unsubstituted or fluorinated $C_{2-20}$ alkyl groups, aryl groups, aminoalkyl groups, $C_{6-22}$ alkoxy groups, a group represented by the formula, $(CH_3)_3SiO[(CH_3)_2SiO]_xSi(CH_3)_2CH_2CH_2$—, and a group represented by the formula, $C_4H_9(CH_3)_2SiO[(CH_3)_2SiO]_xSi(CH_3)_2CH_2CH_2$—, wherein x is an integer of from 0 to 1000, h is an integer of from 0 to 1000, i is an integer of from 0 to 1000 with h+i ranging from 1 to 2000, j and k each are integers of from 1 to 3. In the formula (2), l and m each are integers of from 0 to 8 with l+m ranging from 3 to 8. In the formula (3), $R^6$ is $C_{2-20}$ alkyl group and y is an integer of from 1 to 4.

Examples of $R^5$ include ethyl, propyl, butyl, hexyl, octyl, decyl, dodecyl, tetradecyl, hexadecyl, octadecyl, trifluoropropyl, nonafluorohexyl, heptadecylfluorodecyl, phenyl, aminopropyl, dimethylaminopropyl, aminoethylaminopropyl, stearoxyl, butoxy, ethoxy, propoxy, cetyloxy, milstyloxy, styryl, and α-methylstyryl groups, among which hexyl, octyl, decyl, dodecyl, tetradecyl, hexadecyl, octadecyl, trifluoropropyl, phenyl, aminopropyl, and aminoethylaminopropyl groups are preferred.

Examples of the silicone oil include liquid organopolysiloxanes having a viscosity of from 0.65 to 10000=$^2$/sec, preferably from 0.65 to 1000=$^2$/sec such as dimethylpolysiloxane, methylphenylpolysiloxane, methylhydrogenpolysiloxane and dimethylsiloxane-methylphenylsiloxane copolymer; cyclosiloxanes such as octamethylcyclotetrasiloxane(D4), decamethylcyclopentasiloxane (D5), dodecamethylcyclohexasiloxane (D6), tetramethyltetrahydrogencyclotetrasiloxane (H4), and tetramethyltetraphenylcyclotetrasiloxane; branched silicones such as tristrimethylsiloxymethylsilane (M3T), tetraquistrimethylsiloxysilane (M4Q), tristrimethylsiloxyphenylsilane, tristrimethylsiloxypropylsilane, tristrimethylsiloxyhexylsilane, and tristrimethylsiloxydecylsilane; higher alkoxy-modified silicone such as stearoxysilicone, alkyl-modified silicone, amino-modified silicone, and fluoro-modified silicone.

The hydrocarbon oils may be linear or cyclic. Those which are solid at room temperature such as ceresin and vaseline are not preferred due to their unsatisfactory usability. Examples of the hydrocarbon oils include α-olefin oligomers, light isoparaffin, light liquid isoparaffin, squalane, synthetic squalane, plant squalane, squalene, liquid paraffin, and liquid isoparaffin.

Examples of the ester oils include diisobutyl adipate, 2-hexyldecyl adipate, di-2-heptylundecyl adipate, N-alkyl glycol monoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, isononyl isononanate, neopentyl glycol dicaprirate, triethyl citrate, 2-ethylhexylsuccinate, amyl acetate, ethyl acetate, butyl acetate, isocetyl stearate, butyl stearate, diisopropyl sebacinate, di-2-ethylhexyl sebacinate, cetyl lactate, myristyl lactate, isopropyl palmitate, 2-ethylhexylpalmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyldimethyloctanoate, ethyllaurate, hexyllaurate, 2-octyldodecyl N-lauroyl-L-glutamate, and diisostearyl malate.

Examples of the glyceride oils include acetoglyceryl, glycerol triisooctanoate, glyceryl triisostearate, glyceryl triisopalmitate, glyceryl monostearate, glyceryl di-2-heptylundecanoate, glyceryl trimyristate, and diglyceryl myristyl isostearate.

Examples of the higher fatty acids include undecylenic acid, oleic acid, linoleic acid, linolenic acid, arachidonic acid, eicosapentaenoic acid (EPA), docosahexaenoic acid (DHA), isostearic acid, and lactic acid. Examples of the higher alcohols include oleyl alcohol, isostearyl alcohol, hexyldodecanol, octyl dodecanol, cetostearyl alcohol, 2-decyltetradecinol, and monooleyl glyceryl ether (cerakyl alcohol).

Examples of the animal or plant oils and semi-synthetic oils include avocado oil, almond oil, olive oil, Glycyrrhiza oil, neat's-foot oil, apricot kernel oil, spermacwheat germ oil, sesame oil, rice germ oil, rice bran oil, sasanqua oil, safflower oil, cinnamon oil, squalane, squalene, turtle oil, soybean oil, tea seed oil, camellia oil, evening primrose oil, corn oil, rapeseed oil, Japanese tung oil, germ oil, persic oil, castor oil, hydrogenated castor oil, castor oil fatty acid methylester, sunflower oil, grape oil, jojoba oil, macadamia nut oil, cottonseed oil, cotton wax, tri-coconut oil fatty acid glyceride, peanut oil, liquid lanolin, polyethylene glycol lanolate and egg yolk oil.

A weight ratio of the organopolysiloxane of the present invention and the liquid unctuous agent preferably ranges from 1/20 to 20/1, particularly from 1/10 to 1/1.

The present invention also relates to a cosmetic comprising the present organopolysiloxane, hereinafter referred to as the component (a). The organopolysiloxane may be incorporated in the composition in the form or the aforesaid paste composition. The cosmetic may comprise at least any one of the components selected from the group consisting of (B) an unctuous agent, (C) water, (D) a compound having an alcoholic hydroxyl group, (E) water soluble or water swellable polymer, (F) powder, (G) a surfactant, (H) a conventional silicone resin, and (I) a composition consisting of a known crosslinked organopolysiloxane and a liquid oil.

The unctuous agent (B) may be any solid, semi-solid, or liquid unctuous agent used for ordinary cosmetics. Examples of the liquid unctuous oil include those listed as the liquid unctuous agent used for the aforesaid paste composition. Other liquid unctuous agent as listed above and a mixture thereof can be used, too.

Examples of the other unctuous agent include animal or plant oils and semisynthetic oils such as linseed oil, Ibota wax, perilla oil, cacao butter, kapok wax, kaya oil, carnauba wax, candelilla wax, beef tallow, beef bone fat, hydrogenated beef tallow, spermaceti wax, hydrogenated oil, sugar cane wax, shear butter, Chinese tung oil, cinnamon oil, jojoba wax, shellac wax, lard, rice bran oil, germ oil, horse fat, palm oil, palm kernel oil, hydrogenated castor oil, bayberry wax, beeswax, mink oil, Japanese wax, Japanese wax kernel oil, montan wax, coconut oil, hydrogenated coconut oil, mutton tallow, lanolin, hydrogenated lanolin, lanolin alcohol, hard lanolin, isopropyl lanolate, POE lanolin alcohol ether, POE lanolin alcohol acetate, and POE hydrogenated lanolin alcohol ether, wherein "POE" represents polyoxyethylene.

Examples of the hydrocarbon oils include ozokerite, ceresin, paraffin, paraffin wax, polyethylene wax, polyethylenepolypropylene wax, pristane, polyisobutylene, microcrystalline wax and vaseline.

Examples of the higher fatty acids include lauric acid, myristic acid, palmitic acid, stearic acid, behenic acid, isostearic acid, and 12-hydroxystearic acid.

Examples of the higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyl dodecanol, cetostearyl alcohol, 2-decyltetradecinol, cholesterol, phytosterol, POE cholesterol ether, monostearyl glycerin ether (batyl alcohol), and monooleyl glyceryl ether (cerakyl alcohol).

Examples of the silicone oil include trimethylsiloxysilicate and a cyclic siloxane solution thereof.

Examples of the fluorinated oil include perfluoropolyethers, perfluorodecaline, perfluorooctane. The component (B) is incorporated in the cosmetic in an amount of from 1 to 95 wt % based on total weight of the cosmetic.

Water (C) can be incorporated in the cosmetic in an amount of from 1 to 95 wt % based on total weight of the cosmetic.

Examples of the (C) compound having an alcoholic hydroxyl group include lower alcohols such as ethanol and isopropanol, sugar alcohols such as sorbitol and maltose, sterol such as cholesterol, sitosterol, phytosterol, and lanosterol, and polyalcohols such as butylene glycol, propylene glycol, dibutylene glycol, and pentyl glycol, among which water soluble monoalcohols or polyalcohols are frequently used. The component (D) can be incorporated in the cosmetic in an amount of from 0.1 to 98 wt % based on total weight of the cosmetic.

The present cosmetic may contain (E) a water-soluble polymer, water-swellable polymer or a mixture thereof. Examples of the water-soluble or water-swellable polymer include gum Arabic, tragacanth gum, arabinogalactan, locust bean gum (carob gum), guar gum, karayagum, carrageenan, pectin, agar-agar, quince seed (i.e., marmelo), starch from rice, corn, potato or wheat, algae colloid, and trant gum; bacteria-derived polymers such as xanthan gum, dextran, succinoglucan, and pullulan; animal-derived polymers such as collagen, casein, albumin, and gelatin; starch-derived polymers such as carboxymethyl starch and methylhydroxypropyl starch; cellulose polymers such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethyl cellulose, crystalline cellulose, and cellulose powder; alginic acid-derived polymers such as sodium alginate and propylene glycol alginate; vinyl polymers such as polyvinyl methylether, polyvinylpyrrolidone, and carboxyvinyl polymer; polyoxyethylene polymers such as polyethylene glycol; polyoxyethylene/polyoxypropylene copolymers; acrylic polymers such as sodium polyacrylate, polyethyl acrylate, and polyacrylamide; polyethyleneimine; cationic polymers; and inorganic thickening agents such as, bentonite, aluminum magnesium silicate, montmorillonite, videlite, nontronite, saponite, hectorite, and silicic anhydride. Film forming polymers such as polyvinyl alcohol and polyvinylpyrollidone are also included.

A. content of the water-soluble or water-swellable polymer (E) in the cosmetic preferably ranges from 0.1 to 25 mass %, based on total weight of the cosmetic.

As the powder (F), any powder which are commonly used in cosmetics may be used, regardless of the shape such as spherical, spindle forms, acicular, and plate-like; particle size such as fume size, fine particles and pigment grade; and particle structure such as porous and non-porous. Examples of the powder include inorganic powder, organic powder, metal salt powder of surface active agent, colored pigments, pearl pigments, metallic powder pigments, and natural colors and the like.

Examples of the inorganic powder include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic anhydride, aluminum silicate, magnesium silicate, aluminum magnesium silicate, calcium silicate, barium silicate, strontium silicate, metal salts of tungstenic acid, hydroxyapatite, vermiculite, higilite, bentonite, montmorillonite, hectolitre, zeolite, ceramics powder, calcium secondary phosphate, alumina, aluminum hydroxide, boron nitride, and silica.

The organic powder is classified into synthetic powder such as those made of styrene-acrylic copolymer, divinylbenzene-styrene copolymer, vinyl resin, urea resin, phenolic resin, fluorinated resin, silicon resin, acrylic resin, melamine resin, epoxy resin and polycarbonate resin and natural powder such as those made of cellulose, silk, starch, lauroyllysine. Examples of the synthetic powder include polyamide powder, polyester powder, polyethylene powder, polypropylene powder, polystyrene powder, polyurethane, benzoguanamine powder, polymethylbenzoguanamine powder, tetrafluoroethylene powder, polymethylmethacrylate powder, cellulose, silk powder, nylon powder such as Nylon 12 and Nylon 6, spherical powder of crosslinked dimethylsilicone elastomer (Japanese Patent Application Laid-open No. 3-93834), spherical powder of polymethylsylsesquioxane (Japanese Patent Application Laid-open No. 3-47848), spherical powder of crosslinked silicone elastomer coated with polymethylsylsesquioxane (Japanese Patent Application Laid-open No. 7-196815, and 9-20631), and hydrophobic silica.

Examples of metal salt of surface active agent (metal soaps) include zinc stearate, aluminum stearate, calcium stearate, magnesium stearate, zinc myristate, magnesium myristate, zinc cetyl phosphate, calcium cetyl phosphate, and zinc/sodium cetyl phosphate.

Examples of colored pigments include inorganic red pigments such as iron oxide, iron hydroxide, and iron titanate, inorganic brown pigments such as γ-iron oxide, inorganic yellow pigments such as iron oxide yellow and loess, inorganic black pigments such as iron oxide black and carbon black, inorganic violet pigments such as manganese violet and cobalt violet, inorganic green pigments such as chromium hydroxide, chromium oxide, cobalt oxide, and cobalt titanate, inorganic blue pigments such as Prussian blue and ultramarine blue, lakes of tar pigments, lakes of natural dyes, and synthetic resin powder such as a composite of these powder.

Examples of pearl pigments include titanium oxide-coated mica, titanium oxide-coated mica, bismuth oxychloride, titanium oxide-coated bismuth oxychloride, titanium oxide-coated talc, fish scales, and titanium oxide-coated colored mica; metallic powder pigments such as aluminum powder, copper powder and stainless powder.

Examples of tar pigments include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207; and natural pigments such as carminic acid, laccaic acid, carthamin, brazilin, and crocin.

Among these powder, spherical powder of at least partly crosslinked dimethylsilicone elastomer, spherical powder of crosslinked polymethylsylsesquioxane, and spherical powder of crosslinked silicone elastomer coated with polymethylsylsesquioxane are parferred, and powder having fluorinated group can be used for various cosmetics, too.

The powder may be in the form of composite or may be treated with silicone oil, fluorine compound, or surfactant to the extent not to adversely affect the present cosmetic. For example, the powder may or may not be treated beforehand with fluorine compound, silicone resin, silane coupling agent, titanium coupling agent, unctuous agent, N-acyl lysine, polyacrylic acid, metal surfactant, amino acid, inorganic compound; treatment of pendants; plasma treatment, or mechanochemical treatment. Two or more of the treatment may be employed. A content of the powder in the cosmetic preferably ranges from 0.1 to 99 wt % based on total weight of the cosmetic. Particularly, a content of the powder in powder solid cosmetics preferably ranges from 80 to 99 wt %.

As the surfactant (G), any surfactants such as anionic, cationic, nonionic or amphoteric surfactants commonly used in cosmetics can be used.

Examples of the anionic surfactants include fatty acid soaps, such as sodium stearate and triethanolamine palmitate, alkylether carboxylic acids and salts thereof, salts of condensates of amino acids with fatty acids, alkyl sulfonate salts, alkenesulfonates, sulfonates of fatty acid esters, fatty acid amide sulfonates, sulfonate salts of the formalin condensates, salts of alkyl sulfates, salts of secondary higher alcohol sulfates, salts of alkyl/allyl ether sulfates, salts of fatty acid ester sulfates, salts of fatty acid alkylolamide sulfates, and salts of Turkey Red oil salfate, alkyl phosphate salts, ether phosphate salts, alkylallylether phosphate salts, amide phosphate salts, and N-acylamino surfactants.

Examples of the cationic surfactants include amine salts such as alkylamine salts, amine salts of polyamine and amino alcohol fatty acid derivatives, alkyl quaternary ammonium salts, aromatic quaternary ammonium salts, pyridinium salts and imidazolium salts.

Examples of the nonionic surfactants include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ether, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, polyoxyalkylene-modified organopolysiloxane (Japanese Patent No. 2137062, Japanese Patent Application Laid-Open No. 7-330907), polyglycerin-modified organopolysiloxane (Publication of Examined Japanese Patent Application No. 62-34039, Japanese Patent No. 2613124, Japanese Patent No. 2844453, Japanese Patent Application Laid-Open No. 2002-179798), polyoxyalkylene/alkyl-modified organopolysiloxane (Japanese Patent Application Laid-Open No. 61-90732, Japanese Patent Application Laid-Open No. 9-59386), alkanolamide, sugar ethers, and sugar amides.

Examples of the amphoteric surfactants include betaine, aminocarboxylates, and imidazoline derivatives. A content of the surfactant (G) preferably ranges from 0.1 to 20 mass %, more preferably from 0.5 to 10 mass %, based on a total mass of the cosmetic.

Among these surfactants, preferred is a linear, branched or alkyl-modified organopolysiloxane having a polyglycerin residue or polyoxyalkylene group in an amount of from 10 to 70 wt % of molecular weight of the surfactant. A content of the surfactant preferably ranges from 0.1 to 20 wt %, particularly from 0.2 to 10 wt % based on total weight of the cosmetic.

The silicone resin (H) is in the form of gum or solid at room temperature and is soluble in decamethylcyclopentasiloxane. Preferred silicone resin gum is a linear silicone represented by the following formula $(CH_3)_3SiO\{(CH_3)_2SiO\}_u\{(CH_3)R^7SiO\}_vSi(CH_3)_3$ wherein $R^7$ is selected from the group consisting of a methyl group, $C_{6-20}$ alkyl group, amino-, fluorinated and quaternary ammonium substituted alkyl groups having 3 to 15 carbon atoms, u ranges from 1001 to 20,000, and v ranges from 1 to 5,000 with u+v ranges from 2,500 to 25,000.

Preferred solid silicone resins include silicones with network structure expressed as MQ, MDQ, MTQ, MDTQ, TD, TQ, and TDQ wherein M is a trialkylsiloxy unit, $R^1_3 SiO_{0.5}$, D is a diallylsiloxy unit, $R^1_2SiO$, T is a monoalkylsiloxy unit, $R^1SiO_{1.5}$ and Q is tetrafunctional unit, $SiO_2$. More preferably, the silicone resin has a pyrrolidone moiety, long chain alkyl moiety, polyoxyalkylene moiety or fluoroalkyl moiety as those described in the Japanese Patent Application Laid-Open No. 2000-234062, and the Japanese Patent No. 3218872.

Other preferred silicone resin (H) include an acryl/silicone graft or block copolymer as those described in the Japanese Patent No. 2704730, and odorless acryl/silicone graft or block copolymer described in the Japanese Patent Application Laid-Open No. 2000-344829. The acrylic/silicone graft or block copolymer may has in the molecule at least one moiety selected from pyrrolidone residue, long chain alkyl groups, polyoxyalkylene groups, fluoroalkyl groups, and anionic groups such as carboxylic group. The acryl/silicone resin is preferably in the form of semisolid or solid at room temperature.

The silicone resin gum, acryl/silicone resin, solid silicon resin may be in the form of solution dissolved in a solvent such as a low-viscosity silicone oil, a volatile silicone oil, and commonly used organic solvents. The silicone resin (H), in either form, is incorporated in the cosmetic preferably in an amount of from 0.1 to 20 wt %, more preferably from 1 to 10 wt % based on total weight of the cosmetic.

Examples of the composition (I) consisting of a crosslinked organopolysiloxane except the organopolysiloxane of the present invention and a liquid unctuous agent include compositions described in the Japanese Patent Application Laid-Open No. H02-43263, H02-214775, H09-136813, 2001-342255, 2004-824798, the Japanese Patent No. 2631772, International Publication WO 03/20828 and WO 03/24413; crosslinked organopolysiloxanes swollen with a silicone oil such as KSG-6, 16, 15, 16, 17, 18, 21, 24, 210, 710, 1610, all available from Shin-Etsu Chemical Co., Ltd.; crosslinked organopolysiloxanes swollen with a hydrocarbon oil such as KSG-31, 32, 34, 310, 320, 340, 41, 42, 44, 810, 820, 840, all available from Shin-Etsu Chemical Co., Ltd.; and crosslinked organopolysiloxanes swollen with an ester oil such as KSG-33, 330, 43, 830, all available from Shin-Etsu Chemical Co., Ltd. The composition of a crosslinked organopolysiloxane can provide mat finish to prevent greasiness, improve affinity to the skin and prevent color migration.

The composition (I) consisting of a crosslinked organopolysiloxane and a liquid oil is incorporated in the cosmetic preferably in an amount of from 0.1 to 50 wt %, more preferably from 1 to 30 wt % based on total weight of the cosmetic.

In the cosmetic of the present invention, other components that are commonly used in cosmetics can be incorporated in an amount not to adversely affect the cosmetic. Examples of the components include film forming agent, oil-soluble gelling agents, clay minerals modified with organic compounds, resins, moisture retention agents, antiseptics, anti-microbial agents, perfumes, salts, antioxidants, pH regulators, a chelating agents, refreshing agents, an anti-inflammatory agent, skin beautifying components, such as skin whitener, cell activator, rough dry skin improver, blood circulation promoter, skin astringent and anti-seborrheic agent, vitamins, amino acids, nucleic acids, hormones, clathrate compounds and hair fixative.

Examples of the oil-soluble gelling agent include metal soaps, such as aluminum stearate, magnesium stearate and zinc myristate; amino acid derivatives, such as N-lauroyl-L-glutamic acid and α,γ-di-n-butylamine; dextrin fatty acid esters, such as dextrin palmitic acid ester, dextrin stearic acid ester and dextrin 2-ethylhexaminic acid palmitic acid ester; inulin fatty acid esters such as fructooligostearate; sucrose fatty acid esters, such as sucrose palmitic acid ester and sucrose stearic acid ester; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay.

Examples of the antiperspirant include aluminum chlorohydrate, aluminum chloride, aluminum sesquichlorohydrate, zirconium hydroxychloride, aluminum zirconium hydroxychloride, and aluminum zirconium glycine complex.

Examples of the ultraviolet absorbents include ultraviolet absorbents of benzoic acid type, such as p-aminobenzoic acid; those of anthranilic acid type, such as methyl anthranilate; those of salicylic acid type, such as methyl salicylate; those of succinic acid type, such as octyl p-methoxysuccinate; those of benzophenone type, such as 2,4-dihydroxybenzophenone; those of urocanic acid type, such as ethyl urocanate; and those of dibenzoylmethane type, such as 4-t-butyl-4'-methoxydibenzoylmethane. Examples of the ultraviolet absorbing and scattering agents include fine powder of titanium dioxide, fine powder of iron-containing titanium dioxide, fine powder of zinc oxide, fine powder of cerium oxide, and a mixture thereof.

Examples of a moisture retention agent include glycerin, sorbitol, propylene glycol, dipropylene glycol, 1,3-butylene glycol, pentylene glycol, glucose, xylitol, maltitol, polyethylene glycol, hyaluronic acid, chondroitin sulfuric acid, pyrrolidone carboxylate, polyoxyethylene glycoside, and polyoxypropylene methylglycoside.

Examples of the antiseptics include alkyl p-oxybenzoates, benzoic acid, sodium benzoate, sorbic acid, potassium sorbate, and phenoxyethanol may be used. For the antibacterial agents, benzoic acid, salicylic acid, carbolic acid, sorbic acid, paraoxybenzoic acid alkyl esters, parachloromethacresol, hexachlorophene, benzalkonium chloride, chlorohexydine chloride, trichlorocarbanilide and phenoxyethanol.

Examples of the salts include inorganic salts such as sodium salts, potassium salts, magnesium salts, calcium salts, aluminum salts, zirconium salts, and zinc salts of hydrochloric acid, sulfuric acid, carbonic acid, and nitric acid; salts of organic acids such as acetic acid, dehydroacetic acid, citric acid, malic acid, succinic acid, ascorbic acid and stearic acid; salts of amine such as triethanolamine; salts of amino acid such as glutamic acid; salts of hyaluronic acid and chondroitin sulfuric acid, aluminum zirconium glycine complex, and neutralization product formed in the cosmetic comprising an acid and an alkali.

Examples of the antioxidants include tocopherol, butylhydroxyanisole, dibutylhydroxytoluene and phytic acid; examples of the pH regulators include lactic acid, citric acid, glycolic acid, succinic acid, tartaric acid, dl-malic acid, potassium carbonate, sodium hydrogen carbonate and ammonium hydrogen carbonate; examples of the chelating agents include alanine, sodium ethylenediamine tetraacetate, sodium polyphosphate, sodium metaphosphate and phosphoric acid. examples of the refrigerants include L-menthol and camphor; and examples of the anti-inflammatory agents include allantoin, glycyrrhizin and salts thereof, glycyrrhetinic acid and stearyl glycyrrhetinate, tranexamic acid and azulene.

Examples of the skin-beautifying components include whitening agents include placenta extract, arbutin, glutathione and Yukinoshita extract; cell activators, such as royal jelly, photosensitizers, cholesterol derivatives and calf blood extract; rough and dry skin improvers; blood circulation improvers, such as nonylic acid vanillyl amide, benzyl nicotinate, beta-butoxyethyl nicotinate, capsaicin, zingerone, cantharis tincture, ichtammol, caffeine, tannic acid, alpha-borneol, tocopheryl nicotinate, inositol hexanicotinate, cyclandelate, cinnarizine, tolazoline, acetyl choline, verapamil, cepharanthin and gamma-oryzanol; skin astringents, such as zinc oxide and tannic acid; and anti-seborrheic agents, such as sulfur and thianthol.

Examples of the vitamins include vitamin A, such as vitamin A oil, retinol, retinyl acetate and retinyl palmitate; vitamin B, including vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and its derivatives, and vitamin B15 and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitamin E, such as alpha-tocopherol, beta-tocopherol, gamma-tocopherol, dl-alpha-tocopheryl acetate, dl-alpha-tocopheryl nicotinate and dl-alpha-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of the amino acids include glycine, valine, leucine, isoleucine, serine, threonine, phenylaranine, alginine, lysine, aspartic acid, glutamic acid, cystine, cysteine, methionine, and tryptophan; examples of the nucleic acids include deoxyribonucleic acid; and examples of the hormones include estradiol and ethenyl estradiol.

Examples of the polymers for hair setting include amphoteric, anionic, cationic, and nonionic polymers, such as polymers of polyvinyl pyrrolidone type such as polyvinyl pyrrolidone, vinyl pyrrolidone/vinyl acetate copolymers; acidic polymers of vinyl acetate ether type such as methyl vinyl ether/maleic acid anhydride alkyl half ester copolymer; polymers of acidic poly vinyl acetate type such as vinyl acetate/crotonic acid copolymer; acidic acrylic polymers such as (meth)acrylic acid/alkyl (meth)acrylate copolymer, (meth) acrylic acid/alkyl (meth) acrylate/alkyl acrylic amide copolymer, and amphoteric acrylic polymer such as N-methacryloylethyl-N,N-dimethylammonium alpha-N-methylcarboxybetaine/alkylmetahcrylate copolymer, hydroxypropyl (metha)acrylate/butylaminoethyl methacrylate/octyl amide of acrylic acid copolymer. Use is also made of naturally occurring polymers such as cellulose or derivatives thereof, keratin, collagen and derivatives thereof.

The cosmetic include skin care cosmetics such as milky lotion, cream, face cleansing cream, pack, oil liquid, massage materials, beautifying liquid, cleansing agent, deodorant, hand cream, and lip cream; makeup cosmetics, such as makeup base, face powder, liquid foundation, oily foundation, rouge, eye shadow, mascara, eyeliner, eyebrow, and lipstick; and hair cosmetics, such as shampoo, rinse, treatment, and setting agent; antiperspirant cosmetics and UV ray protective cosmetics, such as sunscreen milky lotion or sunscreen cream.

The cosmetic may be in various forms such as liquid, emulsion, cream, solid, paste, gel, powder, pressed, multilayered, mousse, spray, and stick.

EXAMPLES

The present invention will be further explained with reference to the following Examples, but not limited thereto. In the following formulas, "Me" stands for methyl group, "Vi" for vinyl group, "Ph" for phenyl group and "%" for "% by weight" unless otherwise specified. In Examples, viscosities were measured at 25° C.

Example 1

In a reaction vessel were placed 256.2 parts by weight of the methylhydrogenpolysiloxane of the following formula (4), 91.4 parts by weight of the methylvinylpolysiloxane of the following formula (5), to which 0.1 part by weight of a 2 wt % chloroplatinic acid solution in divinyltetramethyldisiloxane was added and stirred for 1 hour at 70 to 80° C. To the reaction mixture obtained, 97.2 parts by weight of the methylvinylpolysiloxane of the following formula (6) and 111.2 parts by weight of dimethylpolysiloxane having a viscosity of 6 mm²/s were added. After stirring for additional 2 hours, a reaction product containing a crosslinked organopolysiloxane was obtained.

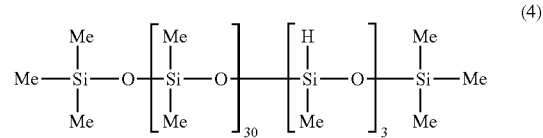

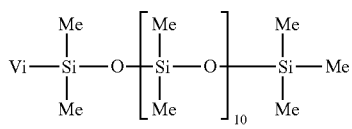

(5)

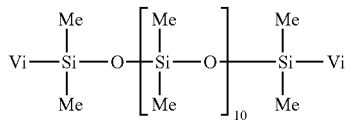

(6)

Using a three-roller mill, 100 parts by weight of the aforesaid product and 220 parts by weight of dimethylpolysiloxane having a viscosity of 6 mm²/s were well kneaded to prepare a paste composition with a weight ratio of the crosslinked organopolysiloxane/dimethylpolysiloxane=25/75.

In a similar manner, 100 parts by weight of the aforesaid product and 300 parts by weight of dimethylpolysiloxane having a viscosity of 6 mm²/s were well kneaded to prepare a paste composition with a weight ratio of the crosslinked organopolysiloxane/dimethylpolysiloxane=20/80.

Comparative Example 1

In a reaction vessel were placed 250.2 parts by weight of the methylhydrogenpolysiloxane of the following formula (7), 97.2 parts by weight of the methylvinylpolysiloxane of the above formula (6), to which 0.1 part by weight of a 2 wt % chloroplatinic acid solution in divinyltetramethyldisiloxane was added. After stirring for 2 hour at 70 to 80° C., a reaction product containing a crosslinked organopolysiloxane was obtained.

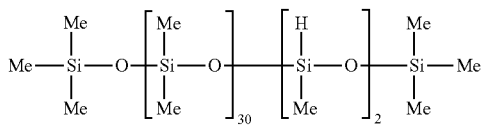

(7)

From the product, a paste composition with a weight ratio of the crosslinked organopolysiloxane/dimethylpolysiloxane having a viscosity of 6 mm²/s=25/75 and 20/80 were prepared in the same manner as in Example 1.

Comparative Example 2

In a reaction vessel were placed 324.2 parts by weight of the methylhydrogenpolysiloxane of the following formula (8), 97.2 parts by weight of the methylvinylpolysiloxane of the above formula (6), and 105.4 parts by weight of dimethylpolysiloxane having a viscosity of 6 mm²/s, to which 0.1 part by weight of a 2 wt % chloroplatinic acid solution in divinyltetramethyldisiloxane was added. After stirring for 2 hour at 70 to 80° C., a reaction product containing a crosslinked organopolysiloxane was obtained.

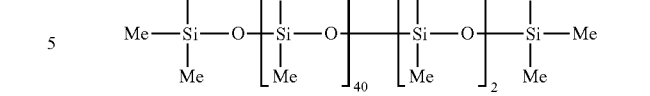

(8)

From the product, a paste composition with a weight ratio of the crosslinked organopolysiloxane/dimethylpolysiloxane having a viscosity of 6 mm²/s=25/75 and 20/80 were prepared in the same manner as in Example 1.

Comparative Example 3

In a reaction vessel 10,000 parts by weight of 10 wt % aqueous solution of hydrochloric acid was placed, to which a mixture of 217.0 parts by weight of trimethylchlorosilane, 5160.0 parts by weight of dimethyldichlorosilane, 230.0 parts by weight of methyldichlorosilane, and 149.5 parts by weight of methyltrichlorosilane was added dropwise in 2 hours while stirring and then stirred for additional 3 hours. The siloxane phase obtained was separated from the aqueous phase containing hydrochloric acid and then washed with water until washing water became neutral. Methylhydrogenpolysiloxane represented by a compositional formula of $M_2 D_{40} T_1 D^H{}_2$ was obtained.

In a reaction vessel were placed 330.9 parts by weight of the methylhydrogenpolysiloxane obtained, 97.2 parts by weight of the methylvinylpolysiloxane of the above formula (6), and 107.0 parts by weight of dimethylpolysiloxane having a viscosity of 6 mm²/s, to which 0.1 part by weight of a 2 wt % chloroplatinic acid solution in divinyltetramethyldisiloxane was added. After stirring for 2 hour at 70 to 80° C., a reaction product containing a crosslinked organopolysiloxane was obtained.

From the product, a paste composition with a weight ratio of the crosslinked organopolysiloxane/dimethylpolysiloxane having a viscosity of 6 mm²/s=25/75 and 20/80 were prepared in the same manner as in Example 1.

Comparative Example 4

In a reaction vessel were placed 256.2 parts by weight of the methylhydrogenpolysiloxane of the above formula (4), 91.4 parts by weight of the methylvinylpolysiloxane of the above formula (5), 97.2 parts by weight of the methylvinylpolysiloxane of the above formula (6), and 111.2 parts by weight of dimethylpolysiloxane having a viscosity of 6 mm²/s, to which 0.1 part by weight of a 2 wt % chloroplatinic acid solution in divinyltetramethyldisiloxane was added. After stirring for 2 hour at 70 to 80° C., a reaction product containing a crosslinked organopolysiloxane was obtained. From the product, paste compositions were prepared in the same manner as in Example 1.

The paste compositions thus prepared were evaluated in viscosity, sensuous properties, and stability of dispersion of titanium oxide. Results are as shown in the Table 1 below, wherein "Ex." stands for Example, and "Comp. Ex." stands for "Comparative Example."

TABLE 1

|  |  | Ex. 1 | Comp. Ex. 1 | Comp. Ex. 2 | Comp. Ex. 3 | Comp. Ex. 4 |
|---|---|---|---|---|---|---|
| Viscosity (mPa·s) | Concentration of the organopolysiloxane 25% | 364,000 | 189,000 | 327,000 | 352,000 | 256,000 |
|  | Concentration of the organopolysiloxane 20% | 85,000 | 5,200 | 10,600 | 39,000 | 9,800 |
| stability of dispersion of titanium oxide[1)] |  | A | C | C | B | C |
| sensuous properties[2)] | sliminess | A | C | D | D | C |
|  | stickiness | A | B | C | D | C |
|  | refreshing feel | A | C | C | C | C |
|  | greasiness | A | B | D | C | C |
|  | lubriciousness | A | A | C | D | B |
|  | cobwebbing | A | B | C | D | C |

1) Test Method for Stability of Titanium Oxide Dispersion

A dispersion was prepared by mixing 70 parts by weight of a paste composition containing 20 wt % of a crosslinked organopolysiloxane and 30 parts by weight of a titanium oxide dispersion consisting of 40 parts by weight of titanium oxide, 10 parts by weight of a acryl silicone dispersant and 50 parts by weight of decamethylcyclopentasiloxane with a DISPER mixer at 2,000 rpm for 5 minutes. The dispersion thus obtained was left stand at room temperature for 1 month and visually observed and rated according to the following criteria:

A: None of the titanium oxide sedimented.
B: A little of the titanium oxide sedimented.
C: Most of the titanium oxide sedimented.

2) Sensuous Properties

Panelists applied on the face skin an amount of a paste composition containing 20 wt % of a crosslinked organopolysiloxane which was touched by a finger, and rated according to the following criteria.

|  | A | B | C | D |
|---|---|---|---|---|
| sliminess | None | A little | Yes | High |
| stickiness | None | A little | Yes | High |
| refreshing feel | High | Average | A little low | None |
| greasiness | None | A little | Yes | High |
| lubriciousness | High | Average | A little | None |
| cobwebbing | None | A little | Yes | Much |

As shown in Table 1 above, in the paste compositions of Example 1, dimethylpolysiloxane having a viscosity of 6 mm²/s was highly thickened to attain high stability of titanium oxide dispersion and good sensuous properties.

The crosslinked organopolysiloxane of Comparative Example 1 which does not have any side chains but has a main chain with the same degree of polymerization and the same molar amount of crosslinkage as that of Example 1 had lower thickening capability than that of Example 1.

As to a viscosity ratio (%) of the composition with 20 wt % of the crosslinked organopolysiloxane to that of the composition with 25 wt % of the crosslinked organopolysiloxane, Example 1 showed a ratio of 23.4%, whereas Comparative Example 1 showed a ratio of 2.8%, indicating larger variation of viscosity with concentration of a crosslinked organopolysiloxane. Comparative Example 1 also showed worse dispersion stability and sensuous properties that that of Example 1.

The crosslinked organopolysiloxane of Comparative Example 2 does not have any side chains but has a main chain with a higher degree of polymerization than that of Example 1. It had a viscosity ratio (%) of the composition with 20 wt % of the crosslinked organopolysiloxane to that of the composition with 25 wt % of the crosslinked organopolysiloxane of 3.2%, indicating larger dependency of viscosity on concentration. It also showed worse dispersion stability and sensuous properties than that of Example 1.

The crosslinked organopolysiloxane of Comparative Example 3 had tri-functional siloxane units in its main chain. It showed a viscosity ratio (%) of the composition with 20 wt % of the crosslinked organopolysiloxane to that of the composition with 25 wt % of the crosslinked organopolysiloxane of 11.1%, which is still smaller than that of Example 1. It showed dispersion stability lower than that of Example 1 and sensuous properties worse than those of Comparative Examples 1 and 2.

In Comparative Example 4, the same starting materials as used in Example 1 were fed simultaneously and subjected to a batch reaction.

The crosslinked organopolysiloxane obtained had lower thickening capability than that of Example 1. Moreover, it showed worse dispersion stability and worse sensuous properties due to a rough and ragged surface.

Example 2

In a reaction vessel were placed 804.2 parts by weight of the methylhydrogenpolysiloxane of the following formula (9), 191.2 parts by weight of the methylvinylpolysiloxane of the following formula (10), to which 0.2 part by weight of a 2 wt % chloroplatinic acid solution in divinyltetramethyldisiloxane was added and stirred for 1 hour at 70 to 80° C. To the reaction mixture obtained, 194.5 parts by weight of the methylvinylpolysiloxane of the above formula (6) was added. After stirring for additional 2 hours, a reaction product containing a crosslinked organopolysiloxane was obtained.

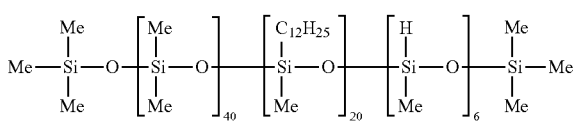

(9)

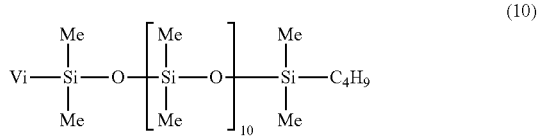

(10)

Using a three-roller mill, the aforesaid reaction product and an unctuous agent selected from dimethylpolysiloxane having a viscosity of 6 mm²/s, liquid paraffin, squalane, glyceryl tri-2-ethylhexanoate and cetyl tri-2-ethylhexanoate were well kneaded to prepare paste compositions containing 30 wt % of the crosslinked organopolysiloxane. The composition had a viscosity as shown in Table 2.

Comparative Example 5

In a reaction vessel were placed 644.2 parts by weight of the methylhydrogenpolysiloxane of the following formula (11), 194.5 parts by weight of the methylvinylpolysiloxane of the above formula (6), to which 0.2 part by weight of a 2 wt % chloroplatinic acid solution in divinyltetramethyldisiloxane was added. After stirring for 2 hour at 70 to 80° C., a reaction product containing a crosslinked organopolysiloxane was obtained.

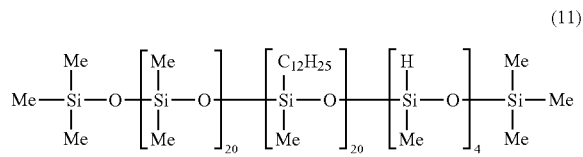

(11)

Comparative Example 6

In a reaction vessel were placed 804.2 parts by weight of the methylhydrogenpolysiloxane of the above formula (9), 191.2 parts by weight of the methylvinylpolysiloxane of the above formula (10), to which 0.2 part by weight of a 2 wt % chloroplatinic acid solution in divinyltetramethyldisiloxane was added. After stirring for 2 hour at 70 to 80° C., a reaction product containing a crosslinked organopolysiloxane was obtained.

Using a three-roller mill, each reaction product and an unctuous agent selected from dimethylpolysiloxane having a viscosity of 6 mm²/s, liquid paraffin, squalane, glyceryl tri-2-ethylhexanoate and cetyl tri-2-ethylhexanoate were well kneaded to prepare paste compositions containing 30 wt % of the crosslinked organopolysiloxane. Table 2 shows viscosity and stability of titanium oxide dispersion tested according to the aforesaid method on each of the compositions.

Example 2. Moreover, it showed worse dispersion stability and worse sensuous properties due to a rough and ragged surface.

Example 3

In a reaction vessel were placed 570.2 parts by weight of the methylhydrogenpolysiloxane of the following formula (12), 274.2 parts by weight of the methylvinylpolysiloxane of the above formula (5), 225.2 parts by weight of dimethylpolysiloxane having a viscosity of 6 mm²/s and 282.3 parts by weight of ethanol, to which 0.2 part by weight of a 3 wt % chloroplatinic acid solution in ethanol was added and stirred for 2 hour at 70 to 80° C. To the reaction mixture obtained, 56.5 parts by weight of the polyoxyethylene diallyl ether of the following formula (13) was added. After stirring for additional 2 hours, 100.0 parts by weight of 2 wt % aqueous citric acid solution was added and stirred for additional 2 hours. Then, 87.5 parts by weight of 2 wt % sodium bicarbonate aqueous solution was added. After stirring for 1 hour, volatiles were distilled off at a reduced pressure and a reaction product containing a crosslinked organopolysiloxane was obtained.

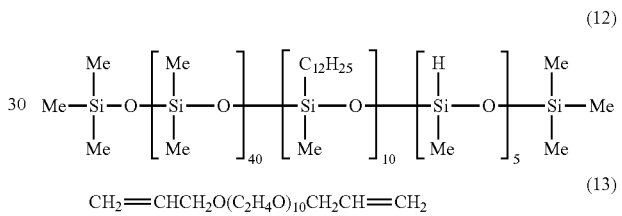

(12)

(13)

Using a three-roller mill, 15 parts by weight of the reaction product and an unctuous agent selected from dimethylpolysiloxane having a viscosity of 6 mm²/s, liquid paraffin,

TABLE 2

| unctuous agent | Example 2 Viscosity (mPa·s) | Example 2 stability of dispersion | Comparative Example 5 Viscosity (mPa·s) | Comparative Example 5 stability of dispersion | Comparative Example 6 Viscosity (mPa·s) | Comparative Example 6 stability of dispersion |
|---|---|---|---|---|---|---|
| dimethylpolysiloxane | 160,000 | A | 10,800 | C | 15,000 | C |
| liquid paraffin | 256,000 | A | 310,000 | A | 203,000 | A |
| squalane | 147,000 | A | 188,000 | A | 89,000 | B |
| glyceryl tri-2-ethylhexanoate | 110,000 | A | 11,200 | C | 96,000 | B |
| cetyl tri-2-ethylhexanoate | 197,000 | A | 218,000 | A | 147,000 | A |

As shown above, the crosslinked organopolysiloxane of Example 2 thickened the silicone oil, hydrocarbon oils, and ester oils, whereas the crosslinked organopolysiloxane of Comparative Example 5 could not thicken the silicone oil or the glycerin ester oil.

In Comparative Example 6, the same starting materials as used in Example 2 were fed simultaneously and subjected to a batch reaction. The crosslinked organopolysiloxane obtained had lower thickening capability than that of squalane, and isotridecyl isononanate in an amount as shown in Table 3 were well kneaded to prepare a paste composition. Table 3 shows viscosity and stability of titanium oxide dispersion tested according to the aforesaid method on each of the compositions.

Comparative Example 7

In a reaction vessel were placed 552.2 parts by weight of the methylhydrogenpolysiloxane of the following formula (14), 56.5 parts by weight of the polyoxyethylene diallyl ether of the above formula (13), 152.2 parts by weight of dimethylpolysiloxane having a viscosity of 6 mm²/s and 172.8 parts by weight of ethanol, to which 0.2 part by weight of 3 wt % chloroplatinic acid solution in ethanol was added. After stirring for 2 hour at 70 to 80° C., 60.0 parts by weight of a 2 wt % aqueous citric acid solution was added and stirred for additional 2 hours. Then, 52.5 parts by weight of a 2 wt % sodium bicarbonate aqueous solution was added. After stirring for 1 hour, volatiles were distilled off at a reduced pressure and a reaction product containing a crosslinked organopolysiloxane was obtained.

acid solution in ethanol was added and stirred for 2 hour at 70 to 80° C. To the reaction mixture obtained, 10.1 parts by weight of triglycerin diallyl ether of the following formula (17) was added. After stirring for additional 2 hours, 40.0 parts by weight of a 2 wt % aqueous citric acid solution was added and stirred for 2 hours. Then, 35.0 parts by weight of a 2 wt % sodium bicarbonate aqueous solution was added. After stirring for 1 hour, volatiles were distilled off at a reduced pressure and a reaction product containing a crosslinked organopolysiloxane was obtained.

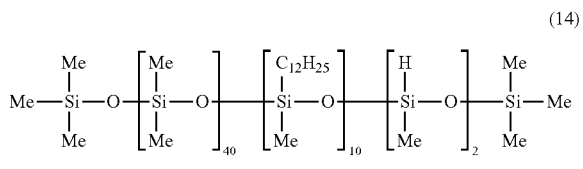

(14)

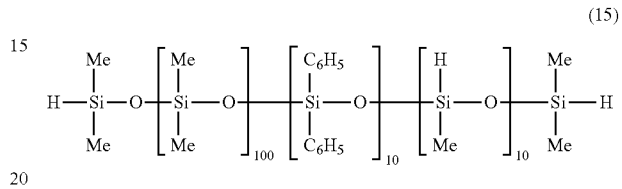

(15)

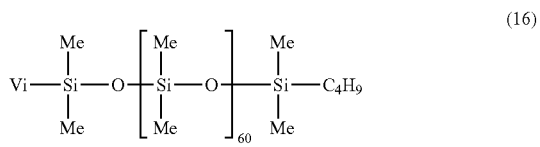

(16)

Using a three-roller mill, 15 parts by weight of the reaction product and an unctuous agent selected from dimethylpolysiloxane having a viscosity of 6 mm²/s, liquid paraffin, squalane, and isotridecyl isononanate in amounts as shown in Table 3 were well kneaded to prepare paste compositions. Table 3 shows viscosity and stability of titanium oxide dispersion tested according to the aforesaid method on each of the compositions.

(17)

$CH_2\!=\!CHCH_2O(CH_2CH(OH)CH_2O)_3CH_2CH\!=\!CH_2$

TABLE 3

| | Example 3 Amount of unctuous agent (parts by weight) | | | Comparative Example 7 Amount of unctuous agent (parts by weight) | | |
|---|---|---|---|---|---|---|
| dimethylpoly siloxane | 35 | 35 | 35 | 35 | 35 | 35 |
| liquid paraffin | 30 | — | — | 30 | — | — |
| squalane | — | 30 | — | — | 30 | — |
| isotridecyl isononanate | — | — | 30 | — | — | 30 |
| Viscosity (mPa · s) | 89,700 | 44,800 | 121,000 | 9,500 | 7,600 | 10,800 |
| stability of dispersion | A | A | A | C | C | B |
| stability of emulsion | A | A | A | C | C | B |

Using a three-roller mill, paste compositions were prepared in the same manner as in Example 3. Viscosity and evaluation results are as shown in Table 4.

Comparative Example 8

In a reaction vessel were placed 390.2 parts by weight of the methylhydrogenpolysiloxane of the following formula (18), 40.3 parts by weight of the triglycerin diallyl ether of the above formula (17), and 42.4 parts by weight of ethanol, to which 0.1 part by weight of 3 wt % chloroplatinic acid solution in ethanol was added. After stirring for 2 hour at 70 to 80° C., 30.0 parts by weight of 2 wt % aqueous citric acid solution was added and stirred for additional 2 hours. Then, 26.2 parts by weight of 2 wt % sodium bicarbonate aqueous solution was added. After stirring for 1 hour, volatiles were distilled off at a reduced pressure and a reaction product containing a crosslinked organopolysiloxane was obtained.

In Table 3, stability of dispersion of each composition was evaluated according to the aforesaid method.

Stability of emulsion was evaluated according to the following method.

A water-in-oil type emulsion was prepared by mixing 30 parts by weight of each paste composition and 70 parts by weight of water by stirring with a DISPER mixer at 3,000 rpm for 5 minutes. The emulsion thus obtained was left stand at 50° C. for 3 weeks and visually observed and rated according to the following criteria:

A: No phase separation is observed.
B: A little phase separation is observed.
C: Phases are nearly completely separated.

Example 4

In a reaction vessel were placed 101.1 parts by weight of the methylhydrogenpolysiloxane of the following formula (15), 279.4 parts by weight of the methylvinylpolysiloxane of the following formula (16), and 117.2 parts by weight of ethanol, to which 0.1 part by weight of 3 wt % chloroplatinic

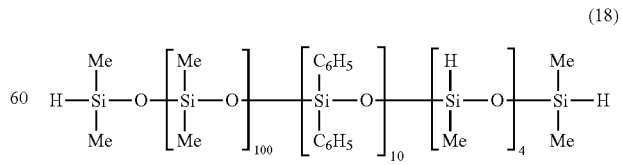

(18)

Using a three-roller mill, paste compositions were prepared in the same manner as in Comparative Example 7. Viscosity and evaluation results are as shown in Table 4.

TABLE 4

|  | Ex.4 Amount (parts by weight) | | | | Comp. Ex. 8 Amount (parts by weight) | | | |
|---|---|---|---|---|---|---|---|---|
| Organopolysiloxane of Example 4 | 25 | 25 | 25 | 25 | — | — | — | — |
| Organopolysiloxane of Comp. Ex. 8 | — | — | — | — | 25 | 25 | 25 | 25 |
| dimethylpoly siloxane | 45 | 45 | 45 | 45 | 45 | 45 | 45 | 45 |
| liquid paraffin | 30 | — | — | — | 30 | — | — | — |
| isododecane | — | 30 | — | — | — | 30 | — | — |
| cetyl 2-ethyl-hexanoate | — | — | 30 | — | — | — | 30 | — |
| isotridecyl isononanate | — | — | — | 30 | — | — | — | 30 |
| Viscosity (mPa·s) | 78,300 | 164,000 | 111,000 | 148,000 | 8,500 | 11,600 | 9,200 | 9,800 |
| stability of dispersion | A | A | A | A | C | B | C | C |
| stability of emulsion | A | A | A | A | C | B | C | C |

In Table 4, stability of dispersion and emulsion were evaluated according to the aforesaid methods.

Example 5

In a reaction vessel were placed 664.2 parts by weight of the methylhydrogenpolysiloxane of the following formula (19), 182.8 parts by weight of the methylvinylpolysiloxane of the above formula (5), and 200.0 parts by weight of ethanol, to which 0.2 part by weight of a 3 wt % chloroplatinic acid solution in ethanol was added and stirred for 2 hour at 70 to 80° C. To the reaction mixture obtained, 146.0 parts by weight of the methylvinylpolysiloxane of the above formula (6) was added. After stirring for additional 2 hours, volatiles were distilled off at a reduced pressure and a reaction product containing a crosslinked organopolysiloxane was obtained.

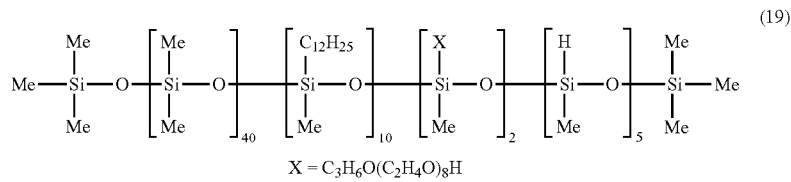

(19)

$X = C_3H_6O(C_2H_4O)_8H$

Example 6

In a reaction vessel were placed 768.2 parts by weight of the methylhydrogenpolysiloxane of the following formula (20), 182.8 parts by weight of the methylvinylpolysiloxane of the above formula (5), and 250.0 parts by weight of ethanol, to which 0.3 part by weight of 3 wt % chloroplatinic acid solution in ethanol was added and stirred for 2 hour at 70 to 80° C. To the reaction mixture obtained, 146.0 parts by weight of the methylvinylpolysiloxane of the above formula (6) was added. After stirring for additional 2 hours, volatiles were distilled off at a reduced pressure and a reaction product containing a crosslinked organopolysiloxane was obtained.

Using a three-roller mill, 25 parts by weight of the reaction products of Examples 5 or 6, and 75 parts by weight of an unctuous agent selected from dimethylpolysiloxane having a viscosity of 6 mm²/s, liquid paraffin, squalane, and glyceryl tri-2-ethylhexanoate were well kneaded to prepare paste composition. The Table below shows viscosity and stability of titanium oxide dispersion tested according to the aforesaid method on each of the compositions.

| unctuous agent | Viscosity(mPa·s) | |
|---|---|---|
|  | Example 5 | Example 6 |
| dimethylpoly-siloxane | 210,000 | 255,000 |

-continued

| unctuous agent | Viscosity(mPa·s) | |
|---|---|---|
|  | Example 5 | Example 6 |
| liquid paraffin | 226,000 | 287,000 |
| squalane | 187,000 | 220,000 |
| glyceryl tri-2-ethyl-hexanoate | 240,000 | 262,000 |

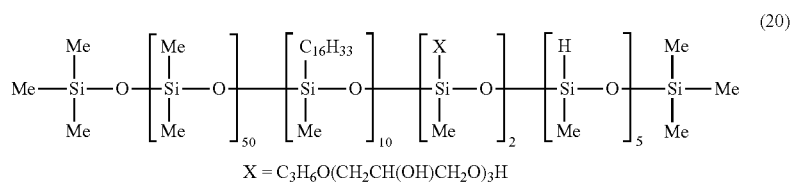

(20)

$X = C_3H_6O(CH_2CH(OH)CH_2O)_3H$

As is found from the above table, the organopolysiloxanes of the Examples 5 and 6 highly thicken all of the unctuous agents.

The following are Examples of the present cosmetics.

Example 7

W/O Type Milky Lotion

| Component | Weight % |
|---|---|
| 1. Composition(1) | 15.0 |
| 2. Dimethylpolysiloxane (6 mm$^2$/sec at 25° C.) | 12.0 |
| 3. Decamethylcyclopentasiloxane | 10.0 |
| 4. Glyceryl trioctanoate | 5.0 |
| 5. Polyether-modified silicone(2) | 3.0 |
| 6. 1,3-butylene glycol | 5.0 |
| 7. Antiseptics | q.s. |
| 8. Perfume | q.s. |
| 9. Purified water | 50.0 |

(1)Composition consisting of 25 parts of the polymer prepared in Example 1 and 75 parts of dimethylpolysiloxane (6 mm$^2$/sec at 25° C.)
(2)KF-6017 from Shin-Etsu Co., Ltd.

Preparation Procedures

A: Components 1 to 5 were mixed.

B: Components 6 to 9 were mixed and the resulting mixture was added to A and emulsified.

The milky lotion thus obtained was non-sticky, spread lightly on the skin and gave a glossy finish having good affinity to the skin.

Example 8

W/O Cream

| Component | Weight % |
|---|---|
| 1. Composition(3) | 6.0 |
| 2. Liquid paraffin | 13.5 |
| 3. Macadamia nuts oil | 4.0 |
| 4. Alkyl/polyether-modified branched type silicone(4) | 1.5 |
| 5. Sodium citrate | 0.2 |
| 6. Propylene glycol | 8.0 |
| 7. Glycerin | 3.0 |
| 8. Antiseptics | q.s. |
| 9. Perfume | q.s. |
| 10. Purified water | 60.8 |

(3)Composition consisting of 30 parts of the polymer prepared in Example 2 and 70 parts of squalane
(4)KF-6038 from Shin-Etsu Co., Ltd.

Preparation Procedures

A: Components 1 to 4 were mixed.

B: Components 5 to 10 were mixed and the resulting mixture was added to A and emulsified.

The cream thus obtained was non-sticky, non-oily, spread lightly on the skin and gave a glossy finish having good affinity to the skin.

Example 9

W/O Type Cream

| Component | Weight % |
|---|---|
| 1. Alkyl-modified crosslinked polyether-modified silicone(5) | 3.0 |
| 2. Composition(6) | 4.0 |
| 3. Liquid paraffin | 13.5 |
| 4. Macadamia nuts oil | 5.0 |
| 5. Alkyl/polyether modified silicone(7) | 0.5 |
| 6. Composite powder of hybrid silicone(8) | 3.0 |
| 7. Sodium citrate | 0.2 |
| 8. Propylene glycol | 8.0 |
| 9. Glycerin | 3.0 |
| 10. Antiseptics | q.s. |
| 11. Perfume | q.s. |
| 12. Purified water | 59.8 |

(5)Alkyl-modified crosslinked polyether-modified silicone; KSG-310 from Shin-Etsu Co., Ltd.
(6)Composition consisting of 30 parts of the polymer prepared in Example 2 and 70 parts of glyceryl tri-2-ethylhexanoate
(7)KF-6038 from Shin-Etsu Co., Ltd.
(8)KSP-100 from Shin-Etsu Co., Ltd.

Preparation Procedures

A: Components 1 to 6 were mixed.

B: Components 7 to 12 were mixed and the resulting mixture was added to A and emulsified.

The W/O type cream thus obtained was non-sticky, non-oily, spread lightly on the skin and gave a mat finish having good affinity to the skin.

Example 10

O/W Type Cream

| Component | Weight % |
|---|---|
| 1. Composition(9) | 8.0 |
| 2. Crosslinked methylphenylpolysiloxane(10) | 2.0 |
| 3. Isotridecyl isononanate | 5.0 |
| 4. Dipropylene glycol | 7.0 |
| 5. Glycerin | 5.0 |
| 6. Methyl cellulose (2% aqueous solution)(11) | 7.0 |
| 7. Polyacrylamide emulsifier(12) | 2.0 |
| 8. Guanine | 1.0 |
| 9. Antiseptics | q.s. |
| 10. Perfume | q.s. |
| 11. Purified water | 63.0 |

(9)Composition consisting of 25 parts of the polymer prepared in Example 1 and 75 parts of dimethylpolysiloxane(20 mm$^2$/s at 25° C.).
(10)KSG-18 from Shin-Etsu Chemical Co., Ltd.
(11)Metholose SM-4000 from Shin-Etsu Chemical Co., Ltd.
(12)Sepigel 305 from SEPIC Preparation Procedures A: Components 3 to 10 were mixed.

B: Components 1 and 2 were mixed and the resulting mixture was added to A and emulsified.

The cream thus obtained had a fine texture. It was non-sticky, non-oily, spread lightly on the skin, and gave a refreshing feel to the skin.

Example 11

W/O Milky Lotion

| Component | Weight % |
|---|---|
| 1. Composition(13) | 10.0 |
| 2. Dimethylpolysiloxane (6 mm$^2$/sec at 25° C.) | 12.0 |
| 3. Decamethylcyclopentasiloxane | 10.0 |
| 4. Isotridecyl isononanate | 5.0 |
| 5. 1,3-butylene glycol | 5.0 |
| 6. Sodium citrate | 0.2 |
| 7. Antiseptics | q.s. |
| 8. Purified water | 58.0 |

(13)Composition consisting of 25 parts of the polymer prepared in Example 3 and 75 parts of dimethylpolysiloxane (6 mm$^2$/sec at 25° C.)

Preparation Procedures

A: Components 1 to 4 were mixed.

B: Components 5 to 8 were mixed and the resulting mixture was added to A and emulsified.

The milky lotion thus obtained was non-sticky, non-oily, spread lightly on the skin, and gave a refreshing feel to the skin and a mat finish having good affinity to the skin.

Example 12

W/O Type Cream

| Component | Weight % |
|---|---|
| 1. Composition(14) | 5.0 |
| 2. Dimethylpolysiloxane (6 mm$^2$/sec at 25° C.) | 10.0 |
| 3. Crosslinked polyether-modified silicone(15) | 2.0 |
| 4. Polyether-modified branched silicone(16) | 0.5 |
| 5. Dipropylene glycol | 10.0 |
| 6. Sodium citrate | 0.2 |
| 7. Ethanol | 5.0 |
| 8. Antiseptics | q.s. |
| 9. Perfume | q.s. |
| 10. Purified water | 67.8 |

(14)Composition consisting of 20 parts of the polymer prepared in Example 1 and 80 parts of decamethylcyclopentasiloxane
(15)KSG-210 from Shin-Etsu Chemical Co., Ltd.
(16)KF-6028 from Shin-Etsu Chemical Co., Ltd.

Preparation Procedures

A: Components 1 to 3 were mixed.

B: Components 4 to 9 were mixed and the resulting mixture was added to A and emulsified.

The cream thus obtained was non-sticky, non-oily, and spread lightly on the skin. It gave a reflshing feel to the skin and a mat finish having good affinity to the skin.

Example 13

W/O Makeup Base

| Component | Weight % |
|---|---|
| 1. Crosslinked polyether-modified silicone(17) | 4.0 |
| 2. Crosslinked dimethylpolysiloxane(18) | 1.0 |
| 3. Composition(19) | 1.0 |
| 4. Polyether-modified branched silicone(20) | 0.5 |
| 5. Dimethylpolysiloxane (6 mm$^2$/ sec at 25° C.) | 6.0 |
| 6. Dimethylpolysiloxane (20 mm$^2$/s at 25° C.) | 2.0 |
| 7. Decamethylcyclopentasiloxane | 3.0 |
| 8. Dispersion of titanium oxide in cyclopentasiloxane(21) | 10.0 |
| 9. Dipropylene glycol | 5.0 |
| 10. Sodium citrate | 0.2 |
| 11. Methyl cellulose (2% aqueous solution)(22) | 2.5 |
| 12. Ethanol | 3.0 |
| 13. Antiseptics | q.s. |
| 14. Perfume | q.s. |
| 15. Purified water | 61.8 |

(17)KSG-210 from Shin-Etsu Chemical Co., Ltd.
(18)KSG-15 from Shin-Etsu Chemical Co., Ltd.
(19)Composition consisting of 20 parts of the polymer prepared in Example 2 and 80 parts of isododecane
(20)KF-6028 from Shin-Etsu Chemical Co., Ltd.
(21)SPD-T5 from Shin-Etsu Chemical Co., Ltd.
(22)Metholose 65-SH4000 from Shin-Etsu Chemical Co., Ltd.

Preparation Procedures

A: Components 1 to 8 were mixed.

B: Components 9 to 15 were mixed and the resulting mixture was added to A and emulsified.

The makeup base thus obtained was non-sticky, non-oily, and spread lightly on the skin. It gave a reflshing feel to the skin and a mat finish having UV-protective effect and good affinity to the skin.

Example 14

O/W Cream

| Component | Weight % |
|---|---|
| 1. Composition(23) | 2.0 |
| 2. Crosslinked dimethylpolysiloxane(24) | 15.0 |
| 3. Decamethylcyclopentasiloxane | 10.0 |
| 4. Dimethylpolysiloxane (6 mm$^2$/sec at 25° C.) | 18.0 |
| 5. Polyether-modified silicone(25) | 0.7 |
| 6. Propylene glycol | 3.0 |
| 7. Polyacrylamide mixture(26) | 0.8 |
| 8. Xanthan gum (2% aqueous solution) | 8.0 |
| 9. Antiseptics | q.s. |
| 10. Perfume | q.s. |
| 11. Purified water | 42.5 |

(23)Composition consisting of 30 parts of the polymer prepared in Example 2 and 70 parts of liquid paraffin.
(24)KSG-16 from Shin-Etsu Chemical Co., Ltd.
(25)KF-6011 from Shin-Etsu Chemical Co., Ltd.
(26)Sepigel 305 from SEPIC Preparation Procedures A: Components 1 to 4 were mixed.

B: Components 5 to 11 were mixed and the resulting mixture was added to A and emulsified.

The cream thus obtained was stable, non-sticky, non-oily, and spread lightly on the skin. It gave a refreshing feel to the skin and stayed long.

Example 15

O/W Cream

| Component | Weight % |
|---|---|
| 1. Composition(27) | 30.0 |
| 2. Composition(28) | 8.0 |
| 3. Decamethylcyclopentasiloxane | 10.0 |
| 4. Polyglycerin-modified branched silicone(29) | 0.6 |
| 5. Polyglycerin-modified branched silicone(30) | 0.3 |
| 6. 1,3-butylene glycol | 3.0 |
| 7. Acrylamide/taurine mixture(31) | 0.6 |
| 8. Ammonium acryloyldimethyltaurine/VP copolymer (5% aqueous solution) | 13.0 |
| 9. Sodium chloride (1% aqueous solution) | 8.0 |
| 10. Purified water | 26.5 |

(27)Composition consisting of 25 parts of the polymer prepared in Example 1 and 75 parts of dimethylpolysiloxane(6 mm$^2$/s at 250° C.).
(28)Composition consisting of 25 parts of the polymer prepared in Example 2 and 75 parts of cetyl 2-ethylhexanoate.
(29)KF-6100 from Shin-Etsu Chemical Co., Ltd.
(30)KF-6104 from Shin-Etsu Chemical Co., Ltd.
(31)Simulgel 600 from SEPIC Preparation Procedures A: Components 1 to 3 were mixed.

B: Components 4 to 10 were mixed and the resulting mixture was added to A and emulsified.

The cream thus obtained was stable and had fine texture because of very small diameter of dispersed oil phase. It was non-sticky, non-oily, and spread lightly on the skin. It gave a refreshing and moisturized feel to the skin.

Example 16

Lipstick

| Component | Weight % |
|---|---|
| 1. Candelilla wax | 4 |
| 2. Polyethylene | 2 |
| 3. Microcrystalline wax | 3 |
| 4. Ceresin | 7 |
| 5. Acrylate/dimethylsilicone copolymer(32) | 15 |
| 6. Composition(33) | 10 |
| 7. Macadamia nuts oil | 30 |
| 8. Diisostearyl malate | 10 |
| 9. Hydrogenated polyisobutene | 15 |
| 10. Isotridecyl isononanate | 4 |
| 11. Pigment base(34) | q.s. |
| 12. Mica | q.s. |
| 13. Perfume | q.s. |

(32)KF-561P from Shin-Etsu Chemical Co., Ltd.
(33)Composition consisting of 30 parts of the polymer prepared in Example 4 and 70 parts of squalane.
(34)60% base in diglyceryl triisostearate Preparation Procedures A: Components 6 to 10 were mixed.

B: Components 1 to 5 were mixed at 90° C. to melt, to which A was mixed.

C: The mixture from B and components 11 to 13 were mixed to be uniform.

The lipstick thus obtained spread lightly on the lips. It was non-powdery, non-oily, and gave a moisturized feel to the lips. The applied lipstick was oil-repellent and resistant to water and durable.

Example 17

Powder Foundation

| Component | Weight % |
|---|---|
| 1. Acrylate/dimethylsilicone copolymer(35) | 3 |
| 2. Squalane | 3 |
| 3. Composition(36) | 6 |
| 4. Mica treated with an acrylsilicone(37) | 50 |
| 5. Talc treated with triethoxycaprylyl(38) | 24 |
| 6. Titanium oxide treated with triethoxyalkylsilicone(39) | 9 |
| 7. Composite powder of hybrid silicone(40) | 2 |
| 8. Powder of spherical polymethylsilsesquioxane(41) | 3 |
| 9. Pigment treated with triethoxyalkylsilicone(42) | q.s. |
| 10. Antiseptics | q.s. |
| 11. Perfume | q.s. |

(35)KP-561P from Shin-Etsu Chemical Co., Ltd.
(36)Composition consisting of 25 parts of the polymer prepared in Example 1 and 75 parts of dimethylpolysiloxane(6 mm$^2$/s at 25° C.)
(37)Treated mica, KP-574 from Shin-Etsu Chemical Co., Ltd.
(38)Treated talc, AES-3083 from Shin-Etsu Chemical Co., Ltd.
(39)Treated titanium oxide, KF-9909 from Shin-Etsu Chemical Co., Ltd.
(40)KSP-300 from Shin-Etsu Chemical Co., Ltd.
(41)KMP-590 from Shin-Etsu Chemical Co., Ltd.
(42)Treated pigment, KF-9909 from Shin-Etsu Chemical Co., Ltd.

Preparation Procedures

A: Components 4 to 10 were mixed.

B: Components 1 to 3 were mixed and added to A.

C: To the mixture from B, component 11 was added and press-molded in a metal mold.

The powder foundation thus obtained was non-sticky to spread smoothly on the skin. It gave a gloss finish with good affinity to the skin.

Example 18

O/W Cream Foundation

| Component | Weight % |
|---|---|
| 1. Composition(43) | 7.0 |
| 2. Composition(44) | 25.0 |
| 3. Acrylate/dimethylsilicone copolymer(45) | 10.0 |
| 4. Polyglycerin-modified branched silicone(46) | 0.9 |
| 5. Polyglycerin-modified branched silicone(47) | 0.3 |
| 6. Polyacrylamide mixture(48) | 1.6 |
| 7. Ammonium acryloyldimethyltaurine/VP copolymer (5% aqueous solution) | 11.0 |
| 8. Sodium chloride(4% aqueous solution) | 2.0 |
| 9. Purified water | 26.8 |
| 10. Polyoxyethylene hydrogenated castor oil | 0.3 |
| 11. Alkyl/polyglycerin-modified branched silicone(49) | 0.1 |
| 12. 1,3-butylene glycol | 5.0 |
| 13. Pigment treated with alkylsilicone(50) | 10.0 |

(43)Composition consisting of 20 parts of the polymer prepared in Example 1 and 80 parts of tristrimethylsiloxymethylsilane
(44)Composition consisting of 30 parts of the polymer prepared in Example 2, 30 parts of squalane, and 40 parts of isododecane
(45)KP-545 from Shin-Etsu Chemical Co., Ltd.
(46)KF-6100 from Shin-Etsu Chemical Co., Ltd.
(47)KF-6104 from Shin-Etsu Chemical Co., Ltd.
(48)Sepigel 310 from SEPIC
(49)KF-6105 from Shin-Etsu Chemical Co., Ltd.
(50)Treated powder, KF-9909 from Shin-Etsu Chemical Co., Ltd.

Preparation Procedures

A: Components 1 to 3, a part of Component 4, and Component 5 were mixed.

B: Components 6 to 9 and a part of Component 10 were mixed.

C: Components 11 to 14, and the rest of Component 4 were mixed and dispersed in the rest of Component 10.

D: The mixture from A was added to the mixture from B.

E: The dispersion from C was added to the mixture from D.

The cream foundation thus obtained was non-sticky to spread smoothly on the skin. The pigments were well dispersed and gave a mat finish with good affinity to the skin.

Example 19

W/O Cream Foundation

| Component | Weight % |
|---|---|
| 1. Composition(51) | 5.0 |
| 2. Composition(52) | 6.0 |
| 3. Polyether-modified silicone(53) | 1.0 |
| 4. Dimethylpolysiloxane (6 mm$^2$/sec at 25° C.) | 3.0 |
| 5. Decamethylcyclopentasiloxane | 9.0 |
| 6. Triethylhexanoin | 5.0 |
| 7. Neopentylglycol dioctanoate | 2.0 |
| 8. Powder of spherical polymethylsilsesquioxane(54) | 1.5 |
| 9. Polyglycerinalkyl-modified branched silicone(55) | 2.0 |
| 10. Pigment treated with alkylsilicone(56) | 5.0 |
| 11. Pentyl glycol | 5.0 |
| 12. Sodium chloride | 0.5 |
| 13. Sodium citrate | 0.2 |
| 14. Antiseptics | q.s. |
| 15. Perfume | q.s. |
| 16. Purified water | 50.0 |

(51)Composition consisting of 25 parts of the polymer prepared in Example 3 and 75 parts of tetraquistrimethylsiloxysilane
(52)Composition consisting of 25 parts of the polymer prepared in Example 1 and 50 parts of dimethylpolysiloxane(6 mm$^2$/s at 25° C.) and 25 parts of octamethyltrisiloxane
(53)KF-6017 from Shin-Etsu Chemical Co., Ltd.
(54)KMP-590 from Shin-Etsu Chemical Co., Ltd.
(55)KF-6105 from Shin-Etsu Chemical Co., Ltd.
(56)KF-9909 from Shin-Etsu Chemical Co., Ltd.

Preparation Procedures

A: Components 1 to 4, a part of Component 5, and Components 6 to 8 were mixed.

B: Components 9, 10 and the rest of Component 5 were mixed.

C: Components 11 to 14, and Component 16 were mixed.

D: The mixture from C was added to the mixture from A and emulsified.

E: Component 15 and the mixture from B were added to the dispersion from D.

The cream foundation thus obtained was non-sticky to spread smoothly on the skin. The pigments were well dispersed and gave a mat finish with good affinity to the skin.

Example 20

W/O Cream Foundation

| Component | Weight % |
|---|---|
| 1. Composition(57) | 2.0 |
| 2. Composition(58) | 2.0 |
| 3. polyether/alkyl-modified branched silicone(59) | 1.0 |
| 4. Triethylhexanoin | 2.0 |

-continued

| Component | Weight % |
|---|---|
| 5. cetyl isooctanoate | 5.0 |
| 6. Isotridecyl isononanate | 9.0 |
| 7. Composite powder of hybrid silicone(60) | 2.0 |
| 8. Poluglycerinalkyl-modified branched silicone(61) | 0.6 |
| 9. Poluglycerinalkyl-modified branched silicone(62) | 0.3 |
| 10. Pigment treated with alkylsilicone(63) | 10.0 |
| 11. 1,3-butyleneglycol | 5.0 |
| 12. Sodium chloride | 0.5 |
| 13. Sodium citrate | 0.2 |
| 14. Antiseptics | q.s. |
| 15. Perfume | q.s. |
| 16. Purified water | 60.4 |

(57)Composition consisting of 30 parts of the polymer prepared in Example 3 and 70 parts of liquid paraffin
(58)Composition consisting of 30 parts of the polymer prepared in Example 2, 20 parts of decamethylcyclopentasiloxane, 20 parts of isododecane, and 30 parts of squalane
(59)KF-6038 from Shin-Etsu Co., Ltd.
(60)KSP-100 from Shin-Etsu Co., Ltd.
(61)KF-6100 from Shin-Etsu Co., Ltd.
(62)KF-6105 from Shin-Etsu Co., Ltd.
(63)Powder treated with KF-9909 from Shin-Etsu Co., Ltd.

Preparation Procedures

A: Components 1 to 7 were mixed.

B: Components 8 to 11 were mixed.

C: Components 12 to 14, and a part of Component 16 were mixed and dissolved.

D: The mixture from B was added to the rest of Component 16.

E: The mixture from C was added to the mixture from A and emulsified.

F: The mixture from D was added to the emulsion from E and emulsified, to which Component 15 was added.

The cream foundation thus obtained was non-sticky to spread smoothly on the skin. The pigments were well dispersed and gave a mat finish with good affinity to the skin.

Example 21

W/O Liquid Foundation

| Component | Weight % |
|---|---|
| 1. Composition(64) | 3.5 |
| 2. Composition(65) | 5.0 |
| 3. Polyether-modified branched silicone(66) | 2.0 |
| 4. Dimethylpolysiloxane (6 mm$^2$/sec at 25° C.) | 6.5 |
| 5. Decamethylcyclopentasiloxane | 21.6 |
| 6. Triethylhexanoin | 5.0 |
| 7. Oragno-modified bentonite | 1.2 |
| 8. Acrylsilicone copolymer Composition(67) | 1.5 |
| 9. Pigment treated with alkylsilicone(68) | 5.0 |
| 10. Dipropylene glycol | 5.0 |
| 11. Sodium citrate | 0.2 |
| 12. Antiseptics | q.s. |
| 13. Perfume | q.s. |
| 14. Purified water | 38.5 |

(64)Composition consisting of 25 parts of the polymer prepared in Example 3 and 75 parts of dimethylpolysiloxane(10 mm$^2$/s)
(65)Composition consisting of 25 parts of the polymer prepared in Example 1, 25 parts of tristrimethylsiloxysilane, 20 parts of octamethyltrisiloxane, and 30 parts of dimethylpolysiloxane(6 mm2/s at 25° C.)
(66)KF-6028 from Shin-Etsu Co., Ltd.
(67)KF-575 from Shin-Etsu Co., Ltd
(68)Powder treated with KF-9909 from Shin-Etsu Co., Ltd.

Preparation Procedures

A: Components 1 to 4, a part of Component 5, Components 6 and Components 7 were mixed.

B: Components 10 to 12, and 14 were mixed.

C: Components 8, 9 and the rest of Component 5 were mixed and dissolved.

D: The mixture from C was added to the mixture from A and emulsified.

E: Component 13 and the mixture from B was added to the mixture from D were added.

The liquid foundation thus obtained was non-sticky to spread smoothly on the skin. The pigments were well dispersed and gave a mat finish with good affinity to the skin. It was stable with time in spite of its low viscosity.

Example 22

W/O Compact Foundation

| Component | Weight % |
| --- | --- |
| 1. Ceresin | 5.5 |
| 2. Microcrystalline wax | 1.0 |
| 3. Liquid paraffin | 4.0 |
| 5. Polypropylene glycol dicaprirate | 3.0 |
| 6. Alkyl/polyether modified silicone(69) | 1.0 |
| 7. Composition(70) | 8.0 |
| 8. Dimethylpolysiloxane (6 mm$^2$/sec at 25° C.) | 15.5 |
| 9. Titanium oxide treated with oil(71) | 10.0 |
| 10. Pigment | q.s. |
| 11. Lecithin | 0.3 |
| 12. Polyoxyethylene sorbitan monooleate | 0.5 |
| 13. Dipropylene glycol | 8.0 |
| 14. Sodium citrate | 0.2 |
| 15. Purified water | Balance |

(69)KF-6038 from Shin-Etsu Co., Ltd.
(70)Composition consisting of 30 parts of the polymer prepared in Example 3, 30 parts of isododecane, and 40 parts of Liquid paraffin
(71)AES-3083 treated titanium oxide from Shin-Etsu Co., Ltd.

Preparation Procedures

A: Components 1 to 8 were mixed while heating.

B: Components 9 to 13 were mixed.

C: Components 14 and 15 were mixed, to which the mixture from B was added and heated.

D: The mixture from C was added to the mixture from A and emulsified. The emulsion obtained was poured in a compact container.

The compact foundation thus obtained was non-oily though containing much unctuous agents and spread smoothly on the skin. It gave refreshing feel and durable finish with good affinity to the skin.

Example 23

W/O Compact Foundation

| Component | Weight % |
| --- | --- |
| 1. Ceresin | 5.5 |
| 2. Steary modified inulin(72) | 2.0 |
| 3. Neopentylglycol dioctanoate | 8.0 |
| 4. Triethylhexanoin | 4.0 |
| 5. Dimethylpolysiloxane (6 mm$^2$/sec at 25° C.) | 11.5 |
| 6. Composition(73) | 4.0 |
| 7. Alkyl/polyether modified silicone(74) | 1.5 |
| 8. Powder of spherical polymethylsilsesquioxane(75) | 1.5 |
| 9. Titanium oxide treated with alkylsilicone(76) | 10.0 |
| 10. Pigment treated with alkylsilicone(77) | q.s. |
| 11. Lecithin | 0.2 |
| 12. Polyoxyethylene sorbitan monooleate | 0.3 |
| 13. Dipropylene glycol | 8.0 |
| 14. Sodium citrate | 0.2 |
| 15. Purified water | Balance |

(72)Inulin ISK from Chiba Flour Milling Co., Ltd.
(73)Composition consisting of 25 parts of the polymer prepared in Example 4 and 75 parts of decamethylcyclopentasiloxane
(74)KF-6038 from Shin-Etsu Co., Ltd.
(75)KMP-590 from Shin-Etsu Co., Ltd.
(76)Titanium oxide treated with AES-3083 from Shin-Etsu Co., Ltd.
(77)AES-3083 treated pigment from Shin-Etsu Co., Ltd.

Preparation Procedures

A: Components 1 to 8 were mixed while heating.

B: Components 9 to 13 were mixed.

C: Components 14 and 15 were mixed, to which the mixture from B was added and heated.

D: The mixture from C was added to the mixture from A and emulsified. The emulsion obtained was poured in a compact container.

The compact foundation thus obtained was non-oily though containing much unctuous agents and spread smoothly on the skin. It gave refreshing feel and durable finish with good affinity to the skin.

Example 24

Eye Shadow

| Component | Weight % |
| --- | --- |
| 1. Sericite | 40 |
| 2. Mica | 10 |
| 3. Talc | Balance |
| 4. Titanium oxide | 10 |
| 5. Titanium oxide fine powder | 5 |
| 6. Magnesium stearate | 3 |
| 7. Pigment | q.s. |
| 8. Octyldodecanol | 3 |
| 9. Dimethylpolysiloxane (6 mm$^2$/sec at 25° C.) | 4 |
| 10. Composition(78) | 6 |
| 11. Antiseptics | q.s. |
| 12. Perfume | |

(78)Composition consisting of 25 parts of the polymer prepared in Example 1, 50 parts of decamethylcyclopentasiloxane, 25 parts of dimethylpolysiloxane(6 mm$^2$/s at 25° C.)

Preparation Procedures

A: Components 8 to 11 were mixed.

B: Components 1 to 7 were mixed, to which the mixture from A is added.

C: Components 12 was added to the mixture from B.

The eye shadow thus obtained was non-sticky and spread smoothly. It gave durable gloss finish with good affinity.

Example 25

Eye Color

| Component | Weight % |
| --- | --- |
| 1. Ethylene glycol distearate | 12.0 |
| 2. Composition(79) | 5.0 |
| 3. Isotridecyl isononanate | 35.0 |
| 4. Candelilla wax | 2.0 |

-continued

| Component | Weight % |
|---|---|
| 5. Lecithin | 0.2 |
| 6. Composite powder of hybrid silicone(80) | 3.0 |
| 7. Pigment treated with alkylsilicone(81) | q.s. |
| 8. Titanium oxide treated with mica | Balance |

(79)Composition consisting of 30 parts of the polymer prepared in Example 2, 30 parts of liquid paraffin and 40 parts of trioctanoin
(80)KF-6038 from Shin-Etsu Co., Ltd.
(81)Titanium oxide treated with AES-3083 from Shin-Etsu Co., Ltd.

Preparation Procedures

A: Components 2 and 3 were mixed.

B: Components 6 to 8 were mixed.

C: Components 1, 4 and 5 were mixed, to which the mixture from A was added.

D: The mixture from C was added to the mixture from B, which were poured in a container.

The eye color thus obtained was non-sticky, non-oily and spread smoothly. It had good usability and gave durable finish with good affinity.

Example 26

Eye Color

| Component | Weight % |
|---|---|
| 1. Composition(82) | 25.0 |
| 2. Dimethylpolysiloxane (6 mm$^2$/sec at 25° C.) | 20.0 |
| 3. Isotridecyl isononanate | 20.0 |
| 4. Stearyl-modified inulin(83) | 10.0 |
| 5. Ceresin | 1.0 |
| 6. Silica | 0.5 |
| 7. Pigment treated with alkylsilicone(84) | 23.5 |

(82)Composition consisting of 25 parts of the polymer prepared in Example 1 and 75 parts of decamethylcyclopentasiloxane
(83)Inulin ISK from Chiba Flour Milling Co., Ltd.
(84)Pigment treated with KF-9909 from Shin-Etsu Co., Ltd.

Preparation Procedures

A: Components 1 and 2 were mixed.

B: Components 6 and 7 were mixed.

C: Components 3 to 5 were mixed, to which the mixture from B was added and heated, and then poured in a container.

The eye color thus obtained was non-sticky, non-oily and spread smoothly. It gave refreshing feel and durable finish with good affinity.

Example 27

Powder Eyebrow

| Component | Weight % |
|---|---|
| 1. Vaseline | 2.5 |
| 2. Dimethylpolysiloxane (6 mm$^2$/sec at 25° C.) | 1.5 |
| 3. Composition(85) | 1.5 |
| 4. Glyceryl trioctanoate | 3.0 |
| 5. Mica treated with silicone(86) | 40.0 |
| 6. Talc treated with silicone(86) | Balance |
| 7. Titanium oxide treated with silicone(86) | 10.0 |
| 8. Barium sulfate treated with silicone(86) | 15.0 |
| 9. Pigment treated with silicone(87) | q.s. |
| 10. Composite powder of hybrid silicone(88) | 1.5 |

-continued

| Component | Weight % |
|---|---|
| 11. Powder of spherical polymethylsilsesquioxane(89) | 2.5 |
| 12. Antiseptics | q.s. |
| 13. Perfume | q.s. |

(85)Composition consisting of 30 parts of the polymer prepared in Example 2, 40 parts of liquid paraffin and 30 parts of isododecane
(86)Powder treated with KF-9901 from Shin-Etsu Co., Ltd.
(87)Pigment treated with KF-990 from Shin-Etsu Co., Ltd.
(88)KSP-100 from Shin-Etsu Co., Ltd.
(89)KMP-590 from Shin-Etsu Co., Ltd.

Preparation Procedures

A: Components 5 and 12 were mixed.

B: Components 1 and 4 were mixed and added to the mixture from A.

C: Components 13 was added to the mixture from B and press molded into a powder eyebrow.

The eyebrow thus obtained was non-sticky, non-oily and spread smoothly. It gave gloss finish with good affinity.

Example 28

Cream Eye Color

| Component | Weight % |
|---|---|
| 1. Composition(90) | 3.5 |
| 2. Composition(91) | 5.0 |
| 3. Polyether-modified branched silicone(92) | 2.0 |
| 4. Dimethylpolysiloxane (6 mm$^2$/sec at 25° C.) | 6.5 |
| 5. Decamethylcyclopentasiloxane | 21.6 |
| 6. Triethylhexanoin | 5.0 |
| 7. Oragno-modified bentonite | 1.2 |
| 8. Acrylsilicone copolymer Composition(93) | 1.5 |
| 9. Pigment treated with alkylsilicone(94) | 5.0 |
| 10. Dipropylene glycol | 5.0 |
| 11. Sodium citrate | 0.2 |
| 12. Antiseptics | q.s. |
| 13. Perfume | q.s. |
| 14. Purified water | 38.5 |

(90)Composition consisting of 25 parts of the polymer prepared in Example 2 and 75 parts of tristrimethylsiloxysilane
(91)Composition consisting of 25 parts of the polymer prepared in Example 1 and 75 parts of dimethylpolysiloxane (6 mm$^2$/s at 25° C.)
(92)KF-6028 from Shin-Etsu Co., Ltd.
(93)KP-575 from Shin-Etsu Co., Ltd.
(94)Powder treated with KF-9909 from Shin-Etsu Co., Ltd.

Preparation Procedures

A: Components 1 to 4, a part of Component 5, Components 6 and 7 were mixed.

B: Components 10 to 12 and 14 were mixed and dissolved.

C: Components 8, 9 and the rest of Component 5 were mixed.

D: The mixture from C was added to the mixture from A and emulsified.

E: Component 13 and the mixture from B were added to the emulsion from C and mixed.

The cream eye color thus obtained was non-sticky, non-oily and spread smoothly. The powders were well dispersed. It gave mat finish with good affinity. It was stable with time, too.

Example 29

Hair Cream

| Component | Weight % |
|---|---|
| 1. Composition(95) | 2.0 |
| 2. Dimethylpolysiloxane (6 mm$^2$/sec at 25° C.) | 5.0 |
| 3. Decamethylcyclopentasiloxane | 8.0 |
| 4. Stearytrimethylammonium chloride | 1.5 |
| 5. Glycerin | 3.0 |
| 6. Propylene glycol | 5.0 |
| 7. Hydroxyethyl cellulose | 0.2 |
| 8. Antiseptics | q.s. |
| 9. Perfume | q.s. |
| 10. Purified water | 75.3 |

(95)Composition consisting of 30 parts of the polymer prepared in Example 3 and 70 parts of dimethylpolysiloxane (50 mm$^2$/s)

Preparation Procedures

A: Components 1 to 3 were mixed.

B: Components 4 to 8 and 10 were mixed and dissolved.

C: The mixture from B was added to the mixture from A and emulsified. The emulsion was cooled, to which Component 9 was added.

The hair cream thus obtained spread smoothly on the hair. It gave softness, smoothness, moisturizing feel, and gloss to the hair.

Example 30

Conditioning Mousse

| Component | Weight % |
|---|---|
| 1. Composition(96) | 0.5 |
| 2. Dimethylpolysiloxane (6 mm$^2$/sec at 25° C.) | 2.0 |
| 3. Crosslinked dimethylpolysiloxane composition(97) | 0.5 |
| 4. Glyceryl trioctanoate | 1.5 |
| 5. Glycerin | 3.0 |
| 6. Stearyl dimethylbenzylammonium chloride | 0.5 |
| 7. Polyoxyethylene hydrogenated castor oil | 0.5 |
| 8. Ethanol | 7.0 |
| 9. Antiseptics | q.s. |
| 10. Perfume | q.s. |
| 11. Purified water | Balance |
| 12. Liquid petroleum gas | 5.0 |

(96)Composition consisting of 30 parts of the polymer prepared in Example 3 and 70 parts of liquid paraffin
(97)KSG-16 from Shin-Etsu Co., Ltd.

Preparation Procedures

A: Components 1 to 4 were mixed.

B: Components 5 to 9 and 11 were mixed and dissolved.

C: The mixture from B was added to the mixture from A and emulsified. The emulsion was cooled, to which Component 10 was added.

D: An aerosol can was filled with the mixture from C to obtain conditioning mousse.

The conditioning mousse thus obtained gave softness, smoothness, moisturizing feel, and mat finish to the hair.

Example 31

Roll-on-Type Antiperspirant

| Component | Weight % |
|---|---|
| 1. Composition(98) | 25 |
| 2. Composition(99) | 15 |
| 3. Dimethylpolysiloxane (6 mm$^2$/sec at 25° C.) | 10 |
| 4. Decamethylcyclopentasiloxane | 30 |
| 5. Aluminum/zirconium tetrachlorohydrate | 20 |
| 6. Perfume | q.s. |

(98)Composition consisting of 25 parts of the polymer prepared in Example 3 and 75 parts of decamethylcyclopentasiloxane
(99)Composition consisting of 25 parts of the polymer prepared in Example 1 and decamethylcyclopentasiloxane Preparation Procedures A: Components 1 to 4 were mixed.

B: To the mixture from A, Components 5 and 6 were added and dispersed.

The roll-on-type antiperspirant thus obtained spread lightly and gave refreshing feel without greasiness. It was stable with time and temperature and had good usability.

Example 32

W/O Type Antiperspirant

| Component | Weight % |
|---|---|
| 1. Composition(100) | 9.0 |
| 2. Decamethylcyclopentasiloxane | 7.0 |
| 3. Glyceryl trioctanoate | 8.0 |
| 4. 1,3-butyleneglycol | 5.0 |
| 5. Sodium citrate | 0.2 |
| 6. Aluminum chlorohydrate | 20.0 |
| 7. Perfume | q.s. |
| 8. Purified water | 50.8 |

(100)Composition consisting of 25 parts of the polymer prepared in Example 4 and 75 parts of decamethylcyclopentasiloxane Preparation Procedures A: Components 1 to 3 were mixed.

B: Components 4, 5 and 8 were mixed, to which Components 6 and 7 were added and dissolved.

C: The mixture from A and the one from B were mixed and emulsified.

The antiperspirant thus obtained spread lightly and gave refreshing feel without greasiness. It was stable with time and temperature and had good usability.

Example 33

W/O Type UV Cut-off Cream

| Component | Weight % |
|---|---|
| 1. Zinc oxide treated with alkylsilicone(101) | 20.0 |
| 2. Alkyl/Glycerin-modified silicone(102) | 12.0 |
| 3. Decamethylcyclopentasiloxane | 20.0 |

-continued

| Component | Weight % |
|---|---|
| 4. Neopentylglycol dioctanoate | 7.0 |
| 5. Composition(103) | 3.0 |
| 6. Composition(104) | 4.0 |
| 7. Alkyl/polyether-modified branched silicone(105) | 1.0 |
| 8. Octyl methoxy cinnamate | 3.0 |
| 9. Sodium citrate | 0.2 |
| 10. Dipropylene glycol | 3.0 |
| 11. Antiseptics | q.s. |
| 12. Perfume | q.s. |
| 13. Purified water | 26.8 |

(101) Zinc oxide treated with KF-9909 from Shin-Etsu Co., Ltd.: KF-9909
(102) KF-6105 from Shin-Etsu Co., Ltd.
(103) Composition consisting of 30 parts of the polymer prepared in Example 3, 30 parts of liquid paraffin, and 40 parts of isododecane
(104) Composition consisting of 25 parts of the polymer prepared in Example 1 and 75 parts of dimethylpolysiloxane (6 mm$^2$/s at 25° C.)
(105) KF-6038 from Shin-Etsu Co., Ltd.

Preparation Procedures

A: Components 4 to 8 and a part of Component 3 were mixed.

B: Components 9-11 and 13 were mixed.

C: Components 1, 2 and the rest of Component 3 were mixed and dispersed.

D: The mixture from B was added to the mixture from A and emulsified.

E: The dispersion from C and Component 12 were added to the emulsion from D and mixed.

The UV cut-off cream thus obtained spread lightly and gave refreshing feel without greasiness, and durable translucent finish. It was stable with time and temperature.

Example 34

W/O Type UV Cut-Off Milky Lotion

| Component | Weight % |
|---|---|
| 1. Dimethylpolysiloxane (6 mm$^2$/sec at 25° C.) | 5.0 |
| 2. Composition(106) | 5.0 |
| 3. Glyceryl trioctanoate | 2.0 |
| 4. Composition(107) | 1.0 |
| 5. Polyether-modified silicone(108) | 1.0 |
| 6. Titanium oxide dispersed in decamethylcyclopentasiloxane(109) | 30.0 |
| 7. Zinc oxide dispersed in decamethylcyclopentasiloxane(110) | 30.0 |
| 8. Dipropylene glycol | 3.0 |
| 9. Sodium citrate | 0.2 |
| 10. Antiseptics | q.s. |
| 11. Perfume | q.s. |
| 12. Purified water | 22.8 |

(106) Composition consisting of 25 parts of the polymer prepared in Example 2 and 75 parts of decamethylcyclopentasiloxane
(107) Composition consisting of 25 parts of the polymer prepared in Example 1 and 75 parts of dimethylpolysiloxane (20 mm$^2$/s)
(108) KF-6017 from Shin-Etsu Co., Ltd.
(109) SPD-T5 from Shin-Etsu Co., Ltd.
(110) SPD-Z5 from Shin-Etsu Co., Ltd.

Preparation Procedures

A: Components 1 to 5 were mixed.

B: Components 8-10 and 12 were mixed and dissolved. The mixture thus obtained was added to the mixture from A.

C: To the mixture from B, Components 6, 7 and 11 were mixed.

The UV cut-off milky lotion thus obtained spread lightly and gave refreshing feel without greasiness, and durable translucent finish. It was stable with time and temperature.

Example 35

W/O Type UV Cut-Off Cream

| Component | Weight % |
|---|---|
| 1. Composition(111) | 2.0 |
| 2. Composition(112) | 3.0 |
| 3. Polyether-modified silicone(113) | 1.0 |
| 4. Neopentylglycol dioctanoate | 2.0 |
| 5. Silica(114) | 0.2 |
| 6. Titanium oxide dispersed in decamethylcyclopentasiloxane(115) | 25.0 |
| 7. Zinc oxide dispersed in decamethylcyclopentasiloxane(116) | 15.0 |
| 8. 1,3-butyleneglycol | 5.0 |
| 9. Sodium citrate | 0.2 |
| 10. Antiseptics | q.s. |
| 11. Sodium chloride | 0.5 |
| 12. Purified water | 46.1 |

(111) Composition consisting of 25 parts of the polymer prepared in Example 5 and 75 parts of dimethylpolysiloxane (6 mm$^2$/s at 25° C.)
(112) Composition consisting of 25 parts of the polymer prepared in Example 1 and 75 parts of dimethylpolysiloxane (6 mm$^2$/s at 25° C.)
(113) KF-6028 from Shin-Etsu Co., Ltd.
(114) AEROSIL 200
(115) SPD-T5 from Shin-Etsu Co., Ltd.
(116) SPD-Z5 from Shin-Etsu Co., Ltd.

Preparation Procedures

A: Components 1 to 7 were mixed.

B: Components 8 to 12 were mixed and dissolved.

C: To the mixture from A, the mixture from B was added and mixed.

The UV cut-off cream thus obtained spread lightly and gave refreshing feel without greasiness, and durable translucent finish. It was stable with time and temperature.

Example 36

W/O Type UV Cut-Off Cream

| Component | Weight % |
|---|---|
| 1. Composition(117) | 2.0 |
| 2. Composition(118) | 4.0 |
| 3. Polyether-modified silicone(119) | 1.5 |
| 4. Neopentylglycol dioctanoate | 2.0 |
| 5. Dimethylpolysiloxane (6 mm$^2$/sec at 25° C.) | 2.0 |
| 6. Silica(120) | 0.5 |
| 7. Titanium oxide dispersed in decamethylcyclopentasiloxane(121) | 25.0 |
| 8. Zinc oxide dispersed in decamethylcyclopentasiloxane(122) | 10.0 |
| 9. Dibutylene glycol | 5.0 |
| 10. Sodium citrate | 0.2 |
| 11. Antiseptics | q.s. |
| 12. Sodium chloride | 0.5 |
| 13. Purified water | 47.3 |

(117) Composition consisting of 30 parts of the polymer prepared in Example 6 and 70 parts of squalane
(118) Composition consisting of 30 parts of the polymer prepared in Example 2 and 70 parts of trioctanoin
(119) KF-6028 from Shin-Etsu Co., Ltd.
(120) Godball E-16C
(121) SPD-T5 from Shin-Etsu Co., Ltd.
(122) SPD-Z5 from Shin-Etsu Co., Ltd.

Preparation Procedures

A: Components 1 to 8 were mixed.

B: Components 9-13 were mixed and dissolved.

C: To the mixture from A, the mixture from B was added and mixed.

The UV cut-off cream thus obtained spread lightly and gave refreshing feel without greasiness, and durable translucent finish. It was stable with time and temperature.

Example 37

O/W Type UV Cut-off Cream

| Component | Weight % |
| --- | --- |
| 1. Crosslinked organopolysiloxane(123) | 5 |
| 2. Cetyl isooctanoate | 6 |
| 3. Composition(124) | 1 |
| 4. Titanium oxide dispersed in decamethylcyclopentasiloxane(125) | 15 |
| 5. Polyether-modified silicone(126) | 1 |
| 6. Polyacrylamide mixture(127) | 2 |
| 7. Propylene glycol | 5 |
| 8. Methyl cellulose (2% aqueous solution)(128) | 5 |
| 9. Antiseptics | q.s. |
| 10. Perfume | q.s. |
| 11. Purified water | 60 |

(123)KSG-18 from Shin-Etsu Co., Ltd
(124)Composition consisting of 25 parts of the polymer prepared in Example 1 and 75 parts of dimethylpolysiloxane (6 mm$^2$/s at 25° C.)
(125)SPD-T5 from Shin-Etsu Co., Ltd.
(126)KF-6011 from Shin-Etsu Co., Ltd.
(127)Sepigel 305 from SEPIC
(128)Metholose SM-4000 from Shin-Etsu Co., Ltd.

Preparation Procedures

A: Components 5-7, 9 and 11 were mixed.

B: Components 1 to 4 were mixed. The mixture obtained was added to the mixture from A and emulsified.

C: Components 8 and 10 were added to the mixture from B.

The UV cut-off cream thus obtained spread smoothly on the skin. It gave refreshing feel without greasiness, and durable translucent finish. It was stable with time and temperature.

Example 38

Nonaqueous Emulsion

| Component | Weight % |
| --- | --- |
| 1. Composition(129) | 30 |
| 2. Decamethylcyclopentasiloxane | 15 |
| 3. dimethylpolysiloxane(6 mm$^2$/s) | 6 |
| 4. Composition(130) | 3 |
| 5. Alkyl/polyglycerin-modified silicone(131) | 1 |
| 6. Dimethyldistearyl ammonium hectorite | 2 |
| 7. 1,3-butyleneglycol | 43 |

(129)Composition consisting of 25 parts of the polymer prepared in Example 1 and 75 parts of dimethylpolysiloxane (6 mm$^2$/s at 25° C.)
(130)Composition consisting of 25 parts of the polymer prepared in Example 4 and 75 parts of dimethylpolysiloxane (6 mm$^2$/s at 25° C.)
(131)KF-6105 from Shin-Etsu Co., Ltd.

Preparation Procedures

A: Components 1 to 6 were mixed.

B: Component 7 was added to the mixture from A and emulsified.

The nonaqueous emulsion thus obtained was stable and spread smoothly on the skin without greasiness to give a moisturized feel.

Example 39

W/O/W Cream

| Component | Weight % |
| --- | --- |
| 1. Composition(132) | 5.0 |
| 2. Cetyl isooctanoate | 5.0 |
| 3. Composition(133) | 1.0 |
| 4. Decamethylcyclopentasiloxane | 5.0 |
| 5. Methyl glucose dioleate | 1.5 |
| 6. Isohexadecane | 3.5 |
| 7. Magnesium sulfate | 0.5 |
| 8. Propylene glycol | 5.0 |
| 9. Purified water | 39.5 |
| 10. Cetyl alcohol | 1.0 |
| 11. PEG-10 Soya sterol | 2.0 |
| 12. Antiseptics | q.s. |
| 13. Perfume | q.s. |
| 14. Purified water | 31.0 |

(132)Composition consisting of 25 parts of the polymer prepared in Example 3 and 75 parts of dimethylpolysiloxane (6 mm$^2$/s at 25° C.)
(133)Composition consisting of 30 parts of the polymer prepared in Example 2 and 70 parts of squalane Preparation Procedures A: Components 7 to 9 were mixed.

B: Components 1 to 6 were mixed, to which the mixture from A was added.

C: Components 10-12 and 14 were mixed, to which the mixture from A was added dropwise and emulsified.

D: To the mixture from C, component 13 was added and mixed.

The cream thus obtained was stable with time and temperature. It was non-sticky and spread smoothly on the skin to give a durable translucent finish.

Example 40

O/W/O Type Milky Lotion

| Component | Weight % |
| --- | --- |
| 1. Composition(134) | 3 |
| 2. Glyceryl triisooctanoate | 15 |
| 3. Composition(135) | 5 |
| 4. Glucose monostearate | 3 |
| 5. Glycerin | 5 |
| 6. 1,3-butyleneglycol | 5 |
| 7. Antiseptics | q.s. |
| 8. Purified water | 60 |
| 9. Macadamia ternifolia | 2 |
| 10. Cetyl alcohol | 2 |
| 11. Perfume | q.s. |

(134)Composition consisting of 25 parts of the polymer prepared in Example 3 and 75 parts of dimethylpolysiloxane (6 mm$^2$/s at 25° C.)
(135)Composition consisting of 25 parts of the polymer prepared in Example 1 and 75 parts of decamethylcyclopentasiloxane Preparation Procedures A: Components 1 to 3 were mixed.

B: Components 4 to 8 were mixed while heating.

C: Components 9-11 were mixed while heating.

D: The mixture from C was added to the mixture from B, while stirring, and emulsified followed by cooling.

E: The dispersion from D was added to the mixture from A, while stirring, and emulsified.

The milky lotion thus obtained spread lightly and gave refreshing feel without greasiness, and durable translucent finish. It was stable with time and temperature.

Example 41

O/W/O Liquid Foundation

| Component | Weight % |
|---|---|
| 1. Composition(136) | 5 |
| 2. Propylene glycol decanoate | 5 |
| 3. Isopropyl myristate | 5 |
| 4. Alkylsilylated Pigment(137) | 10 |
| 5. Egg yolk origin hydrogenated phospholipid | 1 |
| 6. Glycerin | 2 |
| 7. 1,3-butyleneglycol | 10 |
| 8. Antiseptics | q.s. |
| 9. Purified water | 52 |
| 10. Squalane | 3 |
| 11. Composition(138) | 2 |
| 10. Cetyl alcohol | 5 |
| 11. Perfume | q.s. |

(136)Composition consisting of 30 parts of the polymer prepared in Example 3, 40 parts of liquid paraffin, and 30 parts of isododecane
(137)Pigment treated with AES-3083 from Shin-Etsu Co., Ltd
(138)Composition consisting of 30 parts of the polymer prepared in Example 2 and 70 parts of trioctanoin Preparation Procedures A: Components 1 to 3 were mixed.

B: Components 4 to 9 were mixed while heating.

C: Components 10 and 11 were mixed while heating.

D: The mixture from C was added to the mixture from B, while stirring, and emulsified followed by cooling.

E: The dispersion from D was added to the mixture from A while stirring.

The liquid foundation thus obtained spread lightly and gave refreshing feel without greasiness, and durable translucent finish. It was stable with time and temperature.

As described above, the present organopolysiloxane thickens both silicone oils and other kinds of oils to form a paste without greasiness. It can also form an emulsion and is suitable for use in cosmetics.

The invention claimed is:

1. A method of preparing an organopolysiloxane having a main chain composed of the following repeating units (I), 2 to 199 side chain units (II) and 1 to 50 crosslinkage units (III) per 100 SiO units in the main chain, provided that the organopolysiloxane has at least 2, on average, crosslinkage units (III),

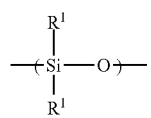
(I)

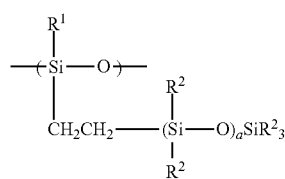
(II)

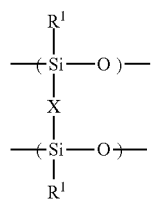
(III)

wherein $R^1$ may be the same with or different from each other and is an organic group selected from the group consisting of substituted or unsubstituted $C_{1\text{-}30}$ hydrocarbon groups having no aliphatic unsaturated bond, a group represented by the formula:

$$-C_jH_{2j}O(C_kH_{2k}O)_bR^4$$

wherein j is an integer of from 2 to 20, k is an integer of from 2 to 4, b is an integer of from 2 to 100, $R^4$ is a hydrogen atom, a substituted or unsubstituted $C_{1\text{-}30}$ hydrocarbon group or an acetyl group, and a group represented by the formula:

$$-C_gH_{2g}OCH_2CH(OH)CH_2O(CH_2CH(OH)CH_2O)_cR^4,$$

wherein g is an integer of from 2 to 20 and c is an integer of from 0 to 10, $R^2$ may be the same with or different from each other and is a substituted or unsubstituted $C_{1\text{-}30}$ hydrocarbon group having no aliphatic unsaturated bond, a is an integer of from 1 to 300, the crosslinkage, X, is selected from the group consisting of an ethylene group and groups represented by the following formula (IV), (V), or (VII)

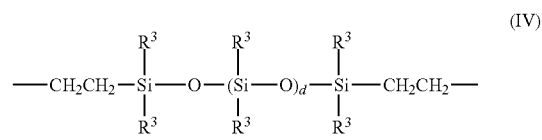
(IV)

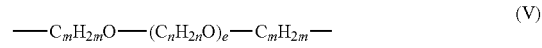
(V)

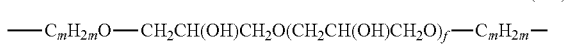
(VII)

wherein $R^3$ may be the same with or different from each other and is a substituted or unsubstituted $C_{1\text{-}30}$ hydrocarbon group having no aliphatic unsaturated bond, d is an integer of from 0 to 500, e is an integer of from 2 to 100, f is an integer of from 0 to 10, m is an integer of from 2 to 20, n is an integer of from 2 to 4, and p is an integer of from 4 to 20, said method comprising the steps of (1) subjecting to an addition reaction an organohydrogenpolysiloxane having at least 3, per molecule, alkylhydrogensiloxane units represented by the formula: —(Si(R$^1$)(H)O)—, and an organovinylpolysiloxane represented by the following formula (XII)

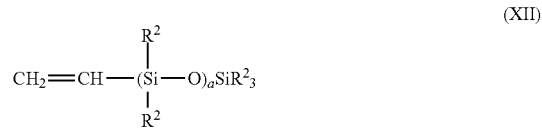
(XII)

wherein $R^1$ may be the same with or different from each other and is selected from the group consisting of substituted or unsubstituted $C_{1\text{-}30}$ hydrocarbon groups having no aliphatic unsaturated bond, a group represented by the formula: $-C_jH_{2j}O(C_kH_{2k}O)_bR^4$ wherein j is an integer of from 2 to 20, k is an integer of from 2 to 4, b is an integer of from 2 to 100, $R^4$ is a hydrogen atom, a substituted or unsubstituted $C_{1\text{-}30}$ hydrocarbon group or an acetyl group, and a group represented by the formula:

$$-C_gH_{2g}OCH_2CH(OH)CH_2O(CH_2CH(OH)CH_2O)_cR^4$$

wherein g is an integer of from 2 to 20 and c is an integer of from 0 to 10, $R^2$ may be the same with or different from each other and is a substituted or unsubstituted $C_{1\text{-}30}$ hydrocarbon group having no aliphatic unsaturated bond, a is an integer of from 1 to 300, and (2) subjecting to a reaction the organohydrogenpolysiloxane obtained in the step (1) and at least one member selected from the group consisting of an organopolysiloxane of the following formula (VIII), a polyoxyalkylene compound of the following formula (IX), and a (poly)glyceryl compound of the following formula (XI)

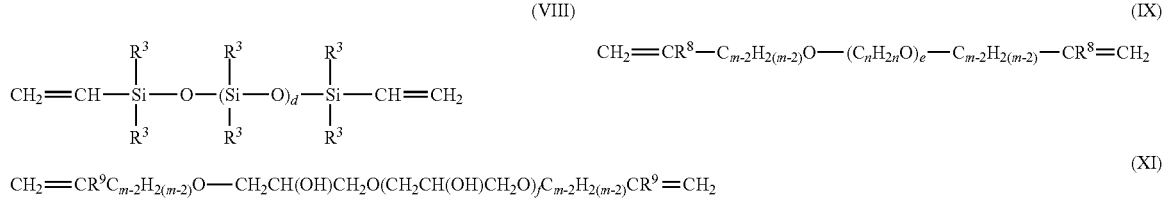

wherein $R^3$, d, e, f, m, and n are as defined above, and $R^8$ and $R^9$ are each a hydrogen atom.

2. The method of claim 1, wherein an inert silicone oil or organic oil is present in the process of producing the siloxane side chain or in the process of producing the crosslinkage.

3. The method of claim 1, wherein the addition reaction is performed in the presence of a platinum compound or a rhodium compound.

4. The method of claim 1, wherein the addition reaction is performed at room temperature or an elevated temperature of 50° C. to 120° C.

5. The method of claim 1, wherein the addition reaction is performed in the absence of a solvent or in the presence of an ethanol or isopropanol solvent.

6. The method of claim 1, wherein the organopolysiloxane is further processed into a paste composition.

7. The method of claim 6, wherein the organopolysiloxane is mixed with an unctuous agent that is liquid at room temperature followed by kneading under shear stress to provide a paste having a smooth appearance.

8. The method of claim 1, wherein at least one of $R^1$ and X contains at least one group selected from polyether groups and polyglyceryl groups.

\* \* \* \* \*